United States Patent
Wei et al.

(10) Patent No.: US 6,664,093 B2
(45) Date of Patent: Dec. 16, 2003

(54) ISOLATED HUMAN ZINC METALLOPROTEASE PROTEINS

(75) Inventors: Ming-Hui Wei, Germantown, MD (US); Chunhua Yan, Germantown, MD (US); Valentina Di Francesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 0 days.

(21) Appl. No.: 10/273,992

(22) Filed: Oct. 21, 2002

(65) Prior Publication Data

US 2003/0129700 A1 Jul. 10, 2003

Related U.S. Application Data

(62) Division of application No. 09/819,989, filed on Mar. 29, 2001, now Pat. No. 6,482,629.

(51) Int. Cl.[7] ............................. C12N 9/64; C12N 9/50; C12N 1/20; C12N 15/00; C07K 1/00
(52) U.S. Cl. .................... 435/226; 435/219; 435/320.1; 435/325; 435/252.3; 435/6; 530/350
(58) Field of Search ................... 435/226, 219, 435/320.1, 325, 252.3, 6; 530/350

(56) References Cited

PUBLICATIONS

Nagase et al., DNA Res., 5, 31–39, 1998.*
Nagase et al. "Predication of the Coding Sequences of Unidentified Human Genes." IX. The Complete Sequences of 100 New cDNA Clones from Brain Which Can Code for Large Proteins in Vitro. DNA Research. Apr. 1998. vol. 5, pp. 31–39.
International Search report dated May 1, 2003.

\* cited by examiner

*Primary Examiner*—Maryam Monshipouri
(74) *Attorney, Agent, or Firm*—Celera Genomics; Justin D. Karjala

(57) ABSTRACT

The present invention provides amino acid sequences of peptides that are encoded by genes within the human genome, the enzyme peptides of the present invention. The present invention specifically provides isolated peptide and nucleic acid molecules, methods of identifying orthologs and paralogs of the enzyme peptides, and methods of identifying modulators of the enzyme peptides.

4 Claims, 15 Drawing Sheets

```
   1 TCGCGGCGGC CGTGATGGCT GGTGACGGCG GGGCCGGGCA GGGGACCGGG
  51 GCCGCGGCCC GGGAGCGGGC CAGCTGCCGG GAGCCCTGAA TCACCGCCTG
 101 GCCCGACTCC ACCATGAACG TCGCGCTGCA GGAGCTGGGA GCTGGCAGCA
 151 ACATGGTGGA GTACAAACGG GCCACGCTTC GGGATGAAGA CGCACCCGAG
 201 ACCCCCGTAG AGGGCGGGGC CTCCCCGGAC GCCATGGAGG TGGGCAAGGG
 251 GGCTTCCCCT TTCTCACCAG GCCCCAGCCC TGGCATGACG CCTGGCACAC
 301 CCAGGAGCTC TGGGCTGTTC TGGAGGGTCA CCTGCCCCCA CCTCCGCTCC
 351 ATCTCTGGCC TCTGCTCTAG GACTATGGTG GGATTCCAGA AGGGGACAAG
 401 ACAGCTGTTA GGCTCACGCA CGCAGCTGGA GCTGGTCTTA GCAGGTGCCT
 451 CTCTACTGCT GGCTGCACTG CTTCTGGGCT GCCTTGTGGC CCTAGGGGTC
 501 CAGTACCACA GAGACCCATC CCACAGCACC TGCCTTACAG AGGCCTGCAT
 551 TCGAGTGGCT GGAAAAATCC TGGAGTCCCT GGACCGAGGG GTGAGCCCCT
 601 GTGAGGACTT TTACCAGTTC TCCTGTGGGG GCTGGATTCG GAGGAACCCC
 651 CTGCCCGATG GCGTTCTCG CTGGAACACC TTCAACAGCC TCTGGGACCA
 701 AAACCAGGCC ATACTGAAGC ACCTGCTTGA AAACACCACC TTCAACTCCA
 751 GCAGTGAAGC TGAGCAGAAG ACACAGCGCT TCTACCTATC TTGCCTACAG
 801 GTGGAGCGCA TTGAGGAGCT GGGAGCCCAG CCACTGAGAG ACCTCATTGA
 851 GAAGATTGGT GGTTGGAACA TTACGGGGCC CTGGGACCAG GACAACTTTA
 901 TGGAGGTGTT GAAGGCAGTA GCAGGGACCT ACAGGGCCAC CCCATTCTTC
 951 ACCGTCTACA TCAGTGCCGA CTCTAAGAGT TCCAACAGCA ATGTTATCCA
1001 GGTGGACCAG TCTGGGCTCT TTCTGCCCTC TCGGGATTAC TACTTAAACA
1051 GAACTGCCAA TGAGAAAGTG CTCACTGCCT ATCTGGATTA CATGGAGGAA
1101 CTGGGGATGC TGCTGGGTGG GCGGCCCACC TCCACGAGGG AGCAGATGCA
1151 GCAGGTGCTG GAGTTGGAGA TACAGCTGGC CAACATCACA GTGCCCCAGG
1201 ACCAGCGGCG CGACGAGGAG AAGATCTACC ACAAGATGAG CATTTCGGAG
1251 CTGCAGGCTC TGGCGCCCTC CATGGACTGG CTTGAGTTCC TGTCTTTCTT
1301 GCTGTCACCA TTGGAGTTGA GTGACTCTGA GCCTGTGGTG GTGTATGGGA
1351 TGGATTATTT GCAGCAGGTG TCAGAGCTCA TCAACCGCAC GGAACCAAGC
1401 ATCCTGAACA ATTACCTGAT CTGGAACCTG GTGCAAAAGA CAACCTCAAG
1451 CCTGGACCGA CGCTTTGAGT CTGCACAAGA GAAGCTGCTG GAGACCCTCT
1501 ATGGCACTAA GAAGTCCTGT GTGCCGAGGT GGCAGACCTG CATCTCCAAC
1551 ACGGATGACG CCCTTGGCTT TGCTTTGGGG TCCCTCTTCG TGAAGGCCAC
1601 GTTTGACCGG CAAAGCAAAG AAATTGCAGA GGGGATGATC AGCGAAATCC
1651 GGACCGCATT TGAGGAGGCC CTGGACAGC TGGTTTGGAT GGATGAGAAG
1701 ACCCGCCAGG CAGCCAAGGA GAAAGCAGAT GCCATCTATG ATATGATTGG
1751 TTTCCCAGAC TTTATCCTGG AGCCCAAAGA GCTGGATGAT GTTTATGACG
1801 GGTACGAAAT TTCTGAAGAT TCTTTCTTCC AAAACATGTT GAATTTGTAC
1851 AACTTCTCTG CCAAGGTTAT GGCTGACCAG CTCCGCAAGC CTCCCAGCCG
1901 AGACCAGTGG AGCATGACCC CCAGACAGT GAATGCCTAC TACCTTCCAA
1951 CTAAGAATGA GATCGTCTTC CCCGCTGGCA TCCTGCAGGC CCCCTTCTAT
2001 GCCCGCAACC ACCCCAAGGC CCTGAACTTC GGTGGCATCG GTGTGGTCAT
2051 GGGCCATGAG TTGACGCATG CCTTTGATGA CCAAGGGCGC GAGTATGACA
2101 AGAAGGGGAA CCTGCGGCCC TGGTGGCAGA ATGAGTCCCT GGCAGCCTTC
2151 CGGAACCACA CGGCCTGCAT GGAGGAACAG TACAATCAAT ACCAGGTCAA
2201 TGGGGAGAGG CTCAACGGCC GCCAGACGCT GGGGGAGAAC ATTGCTGACA
2251 ACGGGGGGCT GAAGGCTGCC TACAATGCTT ACAAAGCATG GCTGAGAAAG
2301 CATGGGGAGG AGCAGCAACT GCCAGCCGTG GGGCTCACCA ACCACCAGCT
2351 CTTCTTCGTG GGATTTGCCC AGGTGTGGTG CTCGGTCCGC ACACCAGAGA
2401 GCTCTCACGA GGGGCTGGTG ACCGACCCCC ACAGCCCTGC CCGCTTCCGC
2451 GTGCTGGGCA CTCTCTCCAA CTCCCGTGAC TTCCTGCGGC ACTTCGGCTG
2501 CCCTGTCGGC TCCCCCATGA ACCCAGGGCA GCTGTGTGAG GTGTGGTAGA
2551 CCTGGATCAG GGGAGAAATG CCCAGCTGTC ACCAGACCTG GGGCAGCTCT
2601 CCTGACAAAG CTGTTTGCTC TTGGGTTGGG AGGAAGCAAA TGCAAGCTGG
2651 GCTGGGTCTA GTCCCTCCCC CCACAGGTG ACATGAGTAC AGACCCTCCT
2701 CAATCACCAC ATTGTGCCTC TGCTTTGGGG GTGCCCCTGC CTCCAGCAGA
2751 GCCCCCACCA TTCACTGTGA CATCTTTCCG TGTCACCCTG CCTGGAAGAG
2801 GTCTGGGTGG GGAGGCCAGT TCCCATAGGA AGGAGTCTGC CTCTTCTGTC
2851 CCCAGGCTCA CTCAGCCTGG CGGCCATGGG GCCTGCCGTG CCTGCCCCAC
2901 TGTGACCCAC AGGCCTGGGT GGTGTACCTC CTGGACTTCT CCCCAGGCTC
2951 ACTCAGTGCG CACTTAGGGG TGGACTCAGC TCTGTCTGGC TCACCCTCAC
3001 GGGCTACCCC CACCTCACCC TGTGCTCCTT GTGCCACTGC TCCCAGTGCT
3051 GCTGCTGACC TTCACTGACA GCTCCTAGTG GAAGCCCAAG GGCCTCTGAA
```

FIGURE 1A

```
3101 AGCCTCCTGC TGCCCACTGT TTCCCTGGGC TGAGAGGGGA AGTGCATATG
3151 TGTAGCGGGT ACTGGTTCCT GTGTCTTAGG GCACAAGCCT TAGCAAATGA
3201 TTGATTCTCC CTGGACAAAG CAGGAAAGCA GATAGAGCAG GGAAAAGGAA
3251 GAACAGAGTT TATTTTTACA GAAAAGAGGG TGGGAGGGTG TGGTCTTGGC
3301 CCTTATAGGA CCCTGTGCCA ATAAACAGAC ATGCATCCGT CAAAAAAAAA
3351 AAAAAAAAAA AAAAAAAAAA AAAAAAA  (SEQ ID NO:1)
```

FEATURES:
5'UTR: 1-113
Start Codon: 114
Stop Codon: 2547
3'UTR: 2550

Homologous proteins:
Top 10 BLAST Hits

|  | Score | E |
|---|---|---|
| CRA\|18000005141003 /altid=gi\|7662200 /def=ref\|NP_055508.1\| KIAA... | 1550 | 0.0 |
| CRA\|18000005084162 /altid=gi\|2136744 /def=pir\|\|I46078 endotheli... | 1430 | 0.0 |
| CRA\|18000005012182 /altid=gi\|1706565 /def=sp\|Q10711\|ECE2_BOVIN ... | 1430 | 0.0 |
| CRA\|150000075554683 /altid=gi\|9789315 /def=gb\|AAF98287.1\|AF2302... | 1027 | 0.0 |
| CRA\|1000682324124 /altid=gi\|5821116 /def=dbj\|BAA83687.1\| (AB031... | 1001 | 0.0 |
| CRA\|108000024636251 /altid=gi\|12721007 /def=ref\|XP_001827.2\| en... | 1001 | 0.0 |
| CRA\|1800004932659 /altid=gi\|627989 /def=pir\|\|A53679 endothelin... | 1000 | 0.0 |
| CRA\|18000005060029 /altid=gi\|1706564 /def=sp\|P42893\|ECE1_RAT EN... | 996 | 0.0 |
| CRA\|18000005155376 /altid=gi\|3287157 /def=emb\|CAA19767.1\| (AL03... | 995 | 0.0 |
| CRA\|18000004985166 /altid=gi\|1082351 /def=pir\|\|JC2521 endotheli... | 995 | 0.0 |

BLAST dbEST hits:

|  | Score | E |
|---|---|---|
| gi\|6837875 /dataset=dbest /taxon=9606 /org=... | 1094 | 0.0 |
| gi\|5925169 /dataset=dbest /taxon=9606 ... | 983 | 0.0 |
| gi\|10725997 /dataset=dbest /taxon=96... | 519 | e-144 |
| gi\|2162041 /dataset=dbest /taxon=9606 ... | 400 | e-109 |

EXPRESSION INFORMATION FOR MODULATORY USE:
library source:
From BLAST dbEST hits:
gi|6837875      lung
gi|5925169      amygdala
gi|10725997     adrenal gland
gi|2162041      total fetus From tissue screening panels:
Hippocampus

FIGURE 1B

```
  1 MNVALQELGA GSNMVEYKRA TLRDEDAPET PVEGGASPDA MEVGKGASPF
 51 SPGPSPGMTP GTPRSSGLFW RVTCPHLRSI SGLCSRTMVG FQKGTRQLLG
101 SRTQLELVLA GASLLLAALL LGCLVALGVQ YHRDPSHSTC LTEACIRVAG
151 KILESLDRGV SPCEDFYQFS CGGWIRRNPL PDGRSRWNTF NSLWDQNQAI
201 LKHLLENTTF NSSSEAEQKT QRFYLSCLQV ERIEELGAQP LRDLIEKIGG
251 WNITGPWDQD NFMEVLKAVA GTYRATPFFT VYISADSKSS NSNVIQVDQS
301 GLFLPSRDYY LNRTANEKVL TAYLDYMEEL GMLLGGRPTS TREQMQQVLE
351 LEIQLANITV PQDQRRDEEK IYHKMSISEL QALAPSMDWL EFLSFLLSPL
401 ELSDSEPVVV YGMDYLQQVS ELINRTEPSI LNNYLIWNLV QKTTSSLDRR
451 FESAQEKLLE TLYGTKKSCV PRWQTCISNT DDALGFALGS LFVKATFDRQ
501 SKEIAEGMIS EIRTAFEEAL GQLVWMDEKT RQAAKEKADA IYDMIGFPDF
551 ILEPKELDDV YDGYEISEDS FFQNMLNLYN FSAKVMADQL RKPPSRDQWS
601 MTPQTVNAYY LPTKNEIVFP AGILQAPFYA RNHPKALNFG GIGVVMGHEL
651 THAFDDQGRE YDKEGNLRPW WQNESLAAFR NHTACMEEQY NQYQVNGERL
701 NGRQTLGENI ADNGGLKAAY NAYKAWLRKH GEEQQLPAVG LTNHQLFFVG
751 FAQVWCSVRT PESSHEGLVT DPHSPARFRV LGTLSNSRDF LRHFGCPVGS
801 PMNPGQLCEV W   (SEQ ID NO:2)
```

FEATURES:
Functional domains and key regions:
[1] PDOC00001 PS00001 ASN_GLYCOSYLATION
N-glycosylation site Number of matches: 9
```
    1      207-210   NTTF
    2      211-214   NSSS
    3      252-255   NITG
    4      312-315   NRTA
    5      357-360   NITV
    6      424-427   NRTE
    7      580-583   NFSA
    8      673-676   NESL
    9      681-684   NHTA
```

[2] PDOC00004 PS00004 CAMP_PHOSPHO_SITE
cAMP- and cGMP-dependent protein kinase phosphorylation site

```
            18-21   KRAT
```

[3] PDOC00005 PS00005 PKC_PHOSPHO_SITE
Protein kinase C phosphorylation site

Number of matches: 8
```
    1       21-23   TLR
    2       62-64   TPR
    3      220-222  TQR
    4      272-274  TYR
    5      340-342  STR
    6      465-467  TKK
    7      582-584  SAK
    8      757-759  SVR
```

[4] PDOC00006 PS00006 CK2_PHOSPHO_SITE
Casein kinase II phosphorylation site

Number of matches: 19
```
    1       21-24   TLRD
    2       30-33   TPVE
    3      103-106  TQLE
    4      161-164  SPCE
    5      192-195  SLWD
```

FIGURE 2A

```
      6     212-215  SSSE
      7     214-217  SEAE
      8     314-317  TANE
      9     340-343  STRE
     10     376-379  SISE
     11     398-401  SPLE
     12     403-406  SDSE
     13     445-448  SSLD
     14     453-456  SAQE
     15     478-481  SNTD
     16     514-517  TAFE
     17     613-616  TKNE
     18     705-708  TLGE
     19     763-766  SSHE
```

[5] PDOC00007 PS00007 TYR_PHOSPHO_SITE
Tyrosine kinase phosphorylation site

```
Number of matches: 4
      1     365-372  RRDEEKIY
      2     457-463  KLLETLY
      3     535-542  KEKADAIY
      4     555-561  KELDDVY
```

[6] PDOC00008 PS00008 MYRISTYL
N-myristoylation site

```
Number of matches: 14
      1       9-14   GAGSNM
      2      57-62   GMTPGT
      3      61-66   GTPRSS
      4     122-127  GCLVAL
      5     159-164  GVSPCE
      6     271-276  GTYRAT
      7     331-336  GMLLGG
      8     335-340  GGRPTS
      9     464-469  GTKKSC
     10     643-648  GVVMGH
     11     714-719  GGLKAA
     12     715-720  GLKAAY
     13     782-787  GTLSNS
     14     795-800  GCPVGS
```

[7] PDOC00047 PS00048 PROTAMINE_P1
Protamine P1 signature

```
             776-787  ARFRVLGTLSNS
```

[8] PDOC00129 PS00142 ZINC_PROTEASE
Neutral zinc metallopeptidases, zinc-binding region signature

```
             645-654  VMGHELTHAF
```

Membrane spanning structure and domains:

| Helix | Begin | End | Score | Certainty |
|---|---|---|---|---|
| 1 | 43 | 63 | 0.638 | Putative |
| 2 | 109 | 129 | 2.142 | Certain |
| 3 | 380 | 400 | 0.619 | Putative |
| 4 | 736 | 756 | 0.890 | Putative |

FIGURE 2B

```
BLAST Alignment to Top Hit:
>CRA|18000005141003 /altid=gi|7662200 /def=ref|NP_055508.1| KIAA0604
        gene product [Homo sapiens] /org=Homo sapiens
        /taxon=9606 /dataset=nraa /length=765
        Length = 765

Score = 1550 bits (3969), Expect = 0.0
 Identities = 765/811 (94%), Positives = 765/811 (94%), Gaps = 46/811 (5%)

Query: 1    MNVALQELGAGSNMVEYKRATLRDEDAPETPVEGGASPDAMEVGKGASPFSPGPSPGMTP 60
            MNVALQELGAGSNMVEYKRATLRDEDAPETPVEGGASPDAMEV
Sbjct: 1    MNVALQELGAGSNMVEYKRATLRDEDAPETPVEGGASPDAMEV----------------- 43

Query: 61   GTPRSSGLFWRVTCPHLRSISGLCSRTMVGFQKGTRQLLGSRTQLELVLAGASLLLAALL 120
                                     GFQKGTRQLLGSRTQLELVLAGASLLLAALL
Sbjct: 44   -------------------------GFQKGTRQLLGSRTQLELVLAGASLLLAALL 74

Query: 121  LGCLVALGVQYHRDPSHSTCLTEACIRVAGKILESLDRGVSPCEDFYQFSCGGWIRRNPL 180
            LGCLVALGVQYHRDPSHSTCLTEACIRVAGKILESLDRGVSPCEDFYQFSCGGWIRRNPL
Sbjct: 75   LGCLVALGVQYHRDPSHSTCLTEACIRVAGKILESLDRGVSPCEDFYQFSCGGWIRRNPL 134

Query: 181  PDGRSRWNTFNSLWDQNQAILKHLLENTTFNSSSEAEQKTQRFYLSCLQVERIEELGAQP 240
            PDGRSRWNTFNSLWDQNQAILKHLLENTTFNSSSEAEQKTQRFYLSCLQVERIEELGAQP
Sbjct: 135  PDGRSRWNTFNSLWDQNQAILKHLLENTTFNSSSEAEQKTQRFYLSCLQVERIEELGAQP 194

Query: 241  LRDLIEKIGGWNITGPWDQDNFMEVLKAVAGTYRATPFFTVYISADSKSSNSNVIQVDQS 300
            LRDLIEKIGGWNITGPWDQDNFMEVLKAVAGTYRATPFFTVYISADSKSSNSNVIQVDQS
Sbjct: 195  LRDLIEKIGGWNITGPWDQDNFMEVLKAVAGTYRATPFFTVYISADSKSSNSNVIQVDQS 254

Query: 301  GLFLPSRDYYLNRTANEKVLTAYLDYMEELGMLLGGRPTSTREQMQQVLELEIQLANITV 360
            GLFLPSRDYYLNRTANEKVLTAYLDYMEELGMLLGGRPTSTREQMQQVLELEIQLANITV
Sbjct: 255  GLFLPSRDYYLNRTANEKVLTAYLDYMEELGMLLGGRPTSTREQMQQVLELEIQLANITV 314

Query: 361  PQDQRRDEEKIYHKMSISELQALAPSMDWLEFLSFLLSPLELSDSEPVVVYGMDYLQQVS 420
            PQDQRRDEEKIYHKMSISELQALAPSMDWLEFLSFLLSPLELSDSEPVVVYGMDYLQQVS
Sbjct: 315  PQDQRRDEEKIYHKMSISELQALAPSMDWLEFLSFLLSPLELSDSEPVVVYGMDYLQQVS 374

Query: 421  ELINRTEPSILNNYLIWNLVQKTTSSLDRRFESAQEKLLETLYGTKKSCVPRWQTCISNT 480
            ELINRTEPSILNNYLIWNLVQKTTSSLDRRFESAQEKLLETLYGTKKSCVPRWQTCISNT
Sbjct: 375  ELINRTEPSILNNYLIWNLVQKTTSSLDRRFESAQEKLLETLYGTKKSCVPRWQTCISNT 434

Query: 481  DDALGFALGSLFVKATFDRQSKEIAEGMISEIRTAFEEALGQLVWMDEKTRQAAKEKADA 540
            DDALGFALGSLFVKATFDRQSKEIAEGMISEIRTAFEEALGQLVWMDEKTRQAAKEKADA
Sbjct: 435  DDALGFALGSLFVKATFDRQSKEIAEGMISEIRTAFEEALGQLVWMDEKTRQAAKEKADA 494

Query: 541  IYDMIGFPDFILEPKELDDVYDGYEISEDSFFQNMLNLYNFSAKVMADQLRKPPSRDQWS 600
            IYDMIGFPDFILEPKELDDVYDGYEISEDSFFQNMLNLYNFSAKVMADQLRKPPSRDQWS
Sbjct: 495  IYDMIGFPDFILEPKELDDVYDGYEISEDSFFQNMLNLYNFSAKVMADQLRKPPSRDQWS 554

Query: 601  MTPQTVNAYYLPTKNEIVFPAGILQAPFYARNHPKALNFGGIGVVMGHELTHAFDDQGRE 660
            MTPQTVNAYYLPTKNEIVFPAGILQAPFYARNHPKALNFGGIGVVMGHELTHAFDDQGRE
Sbjct: 555  MTPQTVNAYYLPTKNEIVFPAGILQAPFYARNHPKALNFGGIGVVMGHELTHAFDDQGRE 614

Query: 661  YDKEGNLRPWWQNESLAAFRNHTACMEEQYNQYQVNGERLNGRQTLGENIADNGGLKAAY 720
            YDKEGNLRPWWQNESLAAFRNHTACMEEQYNQYQVNGERLNGRQTLGENIADNGGLKAAY
Sbjct: 615  YDKEGNLRPWWQNESLAAFRNHTACMEEQYNQYQVNGERLNGRQTLGENIADNGGLKAAY 674
```

FIGURE 2C

```
Query:  721 NAYKAWLRKHGEEQQLPAVGLTNHQLFFVGFAQVWCSVRTPESSHEGLVTDPHSPARFRV 780
             NAYKAWLRKHGEEQQLPAVGLTNHQLFFVGFAQVWCSVRTPESSHEGLVTDPHSPARFRV
Sbjct:  675 NAYKAWLRKHGEEQQLPAVGLTNHQLFFVGFAQVWCSVRTPESSHEGLVTDPHSPARFRV 734

Query:  781 LGTLSNSRDFLRHFGCPVGSPMNPGQLCEVW 811
             LGTLSNSRDFLRHFGCPVGSPMNPGQLCEVW
Sbjct:  735 LGTLSNSRDFLRHFGCPVGSPMNPGQLCEVW 765    (SEQ ID NO:4)
```

Hmmer search results (Pfam):

| Model | Description | Score | E-value | N |
|---|---|---|---|---|
| CE00310 | E00310 neutral_endopeptidase | 456.3 | 2.6e-133 | 1 |
| PF01431 | Peptidase family M13 | 270.4 | 2.4e-77 | 1 |
| CE00339 | E00339 vitamin_D_receptor | 4.3 | 1.1 | 1 |

Parsed for domains:

| Model | Domain | seq-f | seq-t | hmm-f | hmm-t | score | E-value |
|---|---|---|---|---|---|---|---|
| CE00339 | 1/1 | 367 | 398 .. | 412 | 443 .] | 4.3 | 1.1 |
| PF01431 | 1/1 | 607 | 810 .. | 1 | 225 [] | 270.4 | 2.4e-77 |
| CE00310 | 1/1 | 140 | 811 .] | 66 | 798 .] | 456.3 | 2.6e-133 |

FIGURE 2D

```
   1 NNNNNNNNNN NNNNNNNNNN NNNNNNNNNN NNNNNNNNNN NNNNNNNNNN
  51 NNNNNNNNNN NNNNNNNNNN NNNNNNNNNN NNNNNNNNNN NNNNNNNNNN
 101 NNNNNNNNNN NNNNNNNNNN NNNNNNNNNN NNNNNNNNNN NNNNNNNNNN
 151 NNNNNNNNNN NNNNNNNNNN NNNNNNNNNN NNNNNNNNNN NNNNNNNNNN
 201 NNNNNNNNNN NNNNNNNNNN NNNNNNNNNN NNNNNNNNNN NNNNNNNNNN
 251 NNNNNNNNNN NNNNNNNNNN NNNNNNNNNN NNNNNNNNNN NNNNNNNNNN
 301 NNNNNNNNNN NNNNNNNNNN NNNNNNNNNN NNNNNNNNNN NNNNNNNNNN
 351 NNNNNNNNNN NNNNNNNNNN NNNNNNNNNN NNNNNNNNNN NNNNNNNNNN
 401 NNNNNNNNNN NNNNNNNNNN NNNNNNNNNN NNNNNNNNNN NNNNNNNNNN
 451 NNNNNNNNNN NNNNNNNNNN NNNNNNNNNN NNNNNNNNNN NNNNNNNNNN
 501 NNNNNNNNNN NNNNNNNNNN NNNNNNNNNN NNNNNNNNNN NNNNNNNNNN
 551 NNNNNNNNNN NNNNNNNNNN NNNNNNNNNN NNNNNNNNNN NNNNNNNNNN
 601 NNNNNNNNNN NNNNNNNNNN NNNNNNNNNN NNNNNNNNNN NNNNNNNNNN
 651 NNNNNNNNNN NNNNNNNNNN NNNNNNNNNN NNNNNNNNNN NNNNNNNNNN
 701 NNNNNNNNNN NNNNNNNNNN NNNNNNNNNN NNNNNNNNNN NNNNNNNNNN
 751 NNNNNNNNNN NNNNNNNNNN NNNNNNNNNN NNNNNNNNNN NNNNNNNNNN
 801 NNNNNNNNNN NNNNNNNNNN NNNNNNNNNN NNNNNNNNNN NNNNNNNNNN
 851 NNNNNNNNNN NNNNNNNNNN NNNNNNNNNN NNNNNNNNNN NNNNNNNNNN
 901 NNNNNNNNNN NNNNNNNNNN NNNNNNNNNN NNNNNNNNNN NNNNNNNNNN
 951 NNNNNNNNNN NNNNNNNNNN NNNNNNNNNN NNNNNNNNNN NNNNNNNNNN
1001 NNNNNNNNNN NNNNNNNNNN NNNNNNCACC TTAGACTTGA CAGGCCTGCT
1051 TAGTCGGACT CTAAAGCACC CCTTTGCTTT TCGTTAAATA TTGCTTGGTG
1101 TTAGTTTTTT TTCTCCTTGT AAATCTCCCA AATAAACGG TTTGCTTTCC
1151 CCAAGTTAGA AGTGTTAGCA CGTCTTTTCT TTAAATATCT GTGCATGGCT
1201 GTTTTTTTCC CTGCCAATTT GTCACCATCT GTAACCCTCC CTTTATGAGA
1251 CGATCTGATG ACAGCAGTTA TCTTGGAGAG TAGAAGTGTG GTCTTGAAGC
1301 GCCATGGAAG AGTAGAGTCA GTGTATGCTG TGTGTGTGTG GAGTGTATGC
1351 TCCCCCTGCA CTTGGTGTGT GTACATACAG AAACACAGTG TGCGTGTGTG
1401 TTGGCTCTGG GTGTGTTGTG CGTGTGTACA CTGTGTGTGA GTATGCAGTG
1451 TGTGTACATT CTGTGGGCAT CTCGTGTGTG TGTGGACTGT GTGCTGGGCG
1501 TCGTGCCTGC CCGTGTCCTT GGCGCCTTGG CGTCTATGCG TTCTCTGCAC
1551 ATAGGTAGGT ACCACGTGCA CACCCTGAAT GTGAGTGAAC TGCCTGTGTG
1601 CTATGTATTT GCCGGCTGAA GAGGGGCTGT GTGGACTACT GGGGGAAGAC
1651 GTTCCTCANG AGGGCATAAT TTCTCTAAAG TGCTTAAAGG GGATGGAGAG
1701 AGCCTGAAAT TTGGGGGAAG TAGGCCAAGG AGTATTATCA ACGTCTGGGC
1751 CTGGTTGAAT TCATTACTT TTCCTAGGAA AGTAAATTAT GGGTGGCTTG
1801 AAGGAGGGTG CTGCTGAGAT GGGGGGCGGA CCATGAAGCG TGGAGGGGTC
1851 TCCGGTGTTG CTGGAGGGCA GCTGGAGCCT GCGGAGAGCC TCGGCGCGCT
1901 CCTCCCTCTC CCCCACCCTC CCCCCACCCC GGGCGGGGCT CCGCGTGGGG
1951 CGGTGGACTC GGGCGGGGGG GGGGCGGCC GCGGCCGAGC GGGGGTGCTG
2001 CGCGGCGGCC GTGATGGCTG GTGACGGCGG GGCCGGGCAG GGGACCGGGG
2051 CCGCGGCCCG GGAGCGGGCC AGCTGCCGGG AGCCCTGAAT CACCGCCTGG
2101 CCCGACTCCA CCATGAACGT CGCGCTGCAG GAGCTGGGAG CTGGCAGCAA
2151 CGTGAGTGGG GGCCCCGGGC TCCACGGGAG GGGACTGGGT GGAGGGGGAC
2201 GAGGCAGAGG GGTCGGCCGC GGAGGGGCAG GCGGTGCCCG GCTCGCGGAG
2251 GTAAGGCTGC CTCCCGGGCC TGGTGGAGGG GTGATAGAGA GACCCCGGGC
2301 CCGAGAGCAG GGCAGGTGGG AAGGGAAGGG CCCTCTTAGC AGGGCGGAGG
2351 GGTCCGCGAG GCAGGGAGCA CTGGGCAGG GTCGTGGGCA AATAGCCCTC
2401 TCTGCCTGAC CTCGGTTGGC AACCCCGACT GTCTGGCAGA TGGTGGAGTA
2451 CAAACGGGCC ACGCTTCGGG ATGAAGACGC ACCCGAGACC CCCGTAGAGG
2501 GCGGGGCCTC CCCGGACGCC ATGGAGGTGG CAAGGGGGC TTCCCCTTTC
2551 TCACCAGGCC CCAGCCCTGG CATGACGCCT GGCACACCCA GGAGCTCTGG
2601 GCTGTTCTGG AGGGTCATCT GCCCCACCT CCGCTCCATC TCTGGCCTCT
2651 GCTCTAGGAC TATGGTGAGG CGATGCTAAG CCGTGACGTT GCACAAAACA
2701 GACTCAAGGC TCAACTCACT GGCTGGCCTC ATTGCCCCCG GGCCCAGAGT
2751 TAACCCTGTG GCTCTGAAAA CTGCCTGTGG CTTCACCCTC TGGTAATCTT
2801 GGATCCCTGC CCTGCATCTC AGTCACTCTC TGTCCCCCTG TGTTCCCCAG
2851 GTGGGATTCC AGAAGGGGAC AAGACAGCTG TTAGGCTCAC GCACGCAGCT
2901 GGAGCTGGTC TTAGCAGGTG CCTCTCTACT GCTGGCTGCA CTGCTTCTGG
2951 GCTGCCTTGT GGCCCTAGGG GTCCAGTACC ACAGAGGTAG GTGGGCCCAC
3001 ACTCTTCGTC AGTATTCATA ACTAGGGGTT CTGGAGGCCT AAGGGCCTCT
3051 AAGATTTTCA CTTGTGGGAA CCAAGCCTTC CCTGCAGAAA AGCCCCCGGC
```

FIGURE 3A

```
3101 TTTGCTTTCT CTTCCCAACC TTCCTGCTGT CATGGCCCTT GCAGAGTTTG
3151 CCTCTTCCAG ACAGACAGAC TGACAGTCTC CTACCCTCCG GCCATGTTCC
3201 CTACCACAGA CCCATCCCAC AGCACCTGCC TTACAGAGGC CTGCATTCGA
3251 GTGGCTGGAA AAATCCTGGA GTCCCTGGAC CGAGGGGTGA GCCCCTGTGA
3301 GGACTTTTAC CAGTTCTCCT GTGNNNNNNN NNNNNNNNNN NNNNNNNNNN
3351 NNNNNNNNNN NNNNNNNNNN NNNNNNNNNN NNNNNNNNNN NNNNNNNNNN
3401 NNNNNNNNNN NNNNNNNNNN NNNNNNNNNN NNNNNNNNNN NNNNNNNNNN
3451 NNNNNNNNNC TTAGCAAATA GGCAGTGTCC CATGAATGAG GAAGTGGATG
3501 GTTCTGTGAA CACTCCCAGA GGGTGGGGAG GCAGAGAGCA GGGGACTATT
3551 GAGAAGTGCA GATGGGTTTG ATGGGGGCAG AACTCTGGGT ACAATGGAGG
3601 GCCGCTTCTC TGCACTCTGT TTGGAGCACT GTCGTGGTGT GGTAGACACC
3651 AGGGAGCCTG TACTGCTTAG ATATCCTTGG GTCTCCATGG ACAGGGAGAG
3701 GAAGCCACGG CTTGCTGTTT CAGACACTCT TCCTGGGTCT GCGTTAGCAG
3751 GACTGCTCAT TGACAAGGCA AGGAGAGAAA CCGAGCAAGG GCCAGGGACT
3801 CCCCCTCAGC AGTTAACGTA ATTGCCACCT GGATCCTGTG TTCTGCCCCA
3851 CAGAAAACAC CACCTTCAAC TCCAGCAGTG AAGCTGAGCA GAAGACACAG
3901 CGCTTCTACC TATCTTGCCT ACAGGTGGAG CGCATTGAGG AGCTGGGAGC
3951 CCAGCCACTG AGAGACCTCA TTGAGAAGGT AGGGCCACTG AGCCGGTTGA
4001 GGGCAGGGGA GCAGGAGAGG CCTTGAGAGA GGAGATGGCC CAGGAACGCT
4051 TTGGGAGCTC CTGCACTAAT CATTCCACTT ATGGTCTCTA CATAGATTGG
4101 TGGTTGGAAC ATTACGGGGC CCTGGGACCA GGACAACTTT ATGGAGGTGT
4151 TGAAGGCAGT AGCAGGGACC TACAGGGCCA CCCCATTCTT CACCGTCTAC
4201 ATCAGTGCCG ACTCTAAGAG TTCCAACAGC AATGTTATCC AGGTGATGAG
4251 CTGGGAAAGG GTGGGGAGAG ACTTAGGGAC ACTTTGCTGA GCCCAGACTT
4301 CCCTCTCCTG TGACAGGCAG GCTGGGCTGA CCCCCCGGCC CCACCCCTAC
4351 CCCCGCTCGG GAATTCAGGT TCCATGGTG GGGAAAGCGA GGGGCTCACC
4401 TCCTTTCCTT GACATTGCAG GTGGACCAGT CTGGGCTCTT TCTGCCCTCT
4451 CGGGATTACT ACTTAAACAG AACTGCCAAT GAGAAAGTAA GGAACATCTT
4501 CCGAACCCCC ATCCCTACCC CTGGCTGAGC TGGGCTGATC CCTGTTGACT
4551 TTTCCCTTTG CCAAGGGTCA GAGCAGGGAA GGTGAGCCTA TCCTGTCACC
4601 TAGTGAACAA ACTGCCCCTC CTTTCTTTCT TCTTTTCTTC CTCCCTCCCT
4651 CCCTTTCTTC CCCTTTTCCT TCCTTCCTTC CTCTTATTCT TCTAGTAGGT
4701 TTCATAGACA CCTACTGTGT GCCAGGTCCA GTGGGGAAT TCTGAGATAT
4751 AAGTTTNCCG AGCCCATTGC CAGCAGGAGA GGGGATCCTT TAGAGTCGCA
4801 CAAACAGGTC AGTCAAGTCT AAAGACNNNN NNNNNNNNNN NNNNNNNNNN
4851 NNNNNNNNNN NNNNNNNNNN NNNNNNNNNN NNNNNNNNNN NNNNNNNNNN
4901 NNNNNNNNNN NNNNNNNNNN NNNNNNNNNN NNNNNNNNNN NNNNNNNNNN
4951 NNNNNNNNNN NNNNNNNNNN NNNNNNNNNN NNNNNNNNNN NNNNNNNNNN
5001 NNNNNNNNNN NNNNNNNNNN NNNNNNNNNN NNNNNNNNNN NNNNNNNNNN
5051 NNNNNNNNNN NNNNNNNNNN NNNNNNNNNN NNNNNNNNNN NNNNNNNNNN
5101 NNNNNNNNNN NNNNNNNNNN GCCTGNACTT GCATGCACCG CGGTTCGGCT
5151 NCTAGNAGNA TCCCCCCACT GCACTCCAGC CTGGGTGACG GAGAGAGACT
5201 CCGACTCAAA AAAAAAAAAA AAAAGAAAG AAAAAGAAAG AAGGAACAGT
5251 TTAAACAAAA GTGTTGATGA GGCTGAGCAC AGTGGCTCAC ACCTGTAATC
5301 CCCGCACTTT GGGAGGCTGA GGCCGGCGGA TCACTTGAGG TTAGGAGTTC
5351 AAGACCAGGC TGGCCTACAA GGTGAAAACC CGTCTCTACT AAAAATACAA
5401 AAATTAGCCA GGCATGGTGG TGTGCACCTG TAATCTCAGC TACTTGGGAG
5451 GCTGAGGCAA AGAGAATCGC TTGAATCCAG GAGGCAGAGG TTGCAGTGAG
5501 CTGAGATGGC ACCACTGCAC TCCAGCCTGG GCAACAGAAC AAGACTTCAT
5551 CTCAAAAAAA AAAAAAAAAG TGTTGACGAG GAAAGGCTA GGTGTGTCTG
5601 GACCATGGCA AGGGGTCCAC TGTGGTAAAA TATAGAACTC AAGGCAGATG
5651 AGAGGCTGGA GAGGTGGGCA GGAATGGGTT ATGGAGGGGA CCTTGAATAG
5701 CACACTACGG AGTTTATTCT GTAGCTCCCG GAGAGCCATT GCATGCTCCA
5751 AAGTAGGGAG GGAGCGCANT GCTTTGGGAA GTCAGTTTGT TTGGGGTGTG
5801 AAGAGTANAT GTGAGAACNN NNNNNNNNNN NNNNNNNNNN NNNNNNNNNN
5851 NNNNNNNNNN NNNNNNNNNN NNNNNNNNNN NNNNNNNNNN NNNNNNNNNN
5901 NNNNNNNNNN NNNNNNNNNN NNNNNNNNNN NNNNNNNNNN NNNNNNNNNN
5951 NNNNNNNNNN NNNNNNNNNN NNNNNNNNNN NNNNNNNNNN NNNNNNNNNN
6001 NNNNNNNNNN NNNNNNNNNN NNNNNNNNNN NNNNNNNNNN NNNNNNNNNN
6051 NNNNNNNNNN NNNNNNNNNN NNNNNNNNNN NNNNNNNNNN NNNNNNNNNN
6101 NNNNNNNNNN NNNNNNNNNN NNNNNNNNNN NNNNNNNNNN NNNNNNNNNN
6151 NNNNNNNNNN NNNNNNNNNN NNNNNNNNNN NNNNNNNNNN NNNNNNNNNN
```

FIGURE 3B

```
6201 NNNNNNNNNN NNNNNNNNNN NNNNNNNNNN NNNNNNNNNN NNNNNNNNNN
6251 NNNNNNNNNN NNNNNNNNNN NNNNNNNNNN NNNNNNNNNN NNNNNNNNNN
6301 NNNNNNNNNN NNNNNNNNNN NNNNNNNNNN NNNNNNNNNN NNNNNNNNNN
6351 NNNNNNNNNN NNNNNNNNNN NNNNNNNNNN NNNNNNNNNN NNNNNNNNNN
6401 NNNNNNNNNN NNNNNNNNNN NNNNNNNNNN NNNNNNNNNN NNNNNNNNNN
6451 NNNNNNNNNN NNNNNNNNNN NNNNNNNNNN NNNNNNNNNN NNNNNNNNNN
6501 NNNNNNNNNN NNNNNNNNNN NNNNNNNNNN NNNNNNNNNN NNNNNNNNNN
6551 NNNNNNNNNN NNNNNNNNNN NNNNNNNNNN NNNNNNNNNN NNNNNNNNNN
6601 NNNNNNNNNN NNNNNNNNNN NNNNNNNNNN NNNNNNNNNN NNNNNNNNNN
6651 NNNNNNNNNN NNNNNNNNNN NNNNNNNNNN NNNNNNNNNN NNNNNNNNNN
6701 NNNNNNNNNN NNNNNNNNNN NNNNNNNNNN NNNNNNNNNN NNNNNNNNNN
6751 NNNNNNNNNN NNNNNNNNNN NNNNNNNNNN NNNNNNNNNN NNNNNNNNNN
6801 NNNNNNNNNN NNNNNNNNNN NNNNNNNNNN NNNNNNNNNN NNNNNNNNNN
6851 NNNNNNNNNN NNNNNNNNNN NNNNNNNNNN NNNNNNNNNN NNNNNNNNNN
6901 NNNNNNNNNN NNNNNNNNNN NNNNNNNNNN NNNNNNNNNN NNNNNNNNNN
6951 NNNNNNNNNN NNNNNNNNNN NNNNNNNNNN NNNNNNNNNN NNNNNNNNNN
7001 NNNNNNNNNN NNNNNNNNNN NNNNNNNNNN NNNNNNNNNN NNNNNNNNNN
7051 NNNNNNNNNN NNNNNNNNNN NNNNNNNNNN NNNNNNNNNN NNNNNNNNNN
7101 NNNNNNNNNN NNNNNNNNNN NNNNNNNNNN NNNNNNNNNN NNNNNNNNNN
7151 NNNNNNNNNN NNNNNNNNNN NNNNNNNNNN NNNNNNNNNN NNNNNNNNNN
7201 NNNNNNNNNN NNNNNNNNNN NNNNNNNNNN NNNNNNNNNN NNNNNNNNNN
7251 NNNNNNNNNN NNNNNNNNNN NNNNNNNNNN NNNNNNNNNN NNNNNNNNNN
7301 NNNNNNNNNN NNNNNNNNNN NNNNNNNNNN NNNNNNNNNN NNNNNNNNNN
7351 NNNNNNNNNN NNNNNNNNNN NNNNNNNNNN NNNNNNNNNN NNNNNNNNNN
7401 NNNNNNNNNN NNNNNNNNNN NNNNNNNNNN NNNNNNNNNN NNNNNNNNNN
7451 NNNNNNNNNN NNNNNNNNNN NNNNNNNNNN NNNNNNNNNN NNNNNNNNNN
7501 NNNNNNNNNN NNNNNNNNNN NNNNNNNNNN NNNNNNNNNN NNNNNNNNNN
7551 NNNNNNNNNN NNNNNNNNNN NNNNNNNNNN NNNNNNNNNN NNNNNNNNNN
7601 NNNNNNNNNN NNNNNNNNNN NNNNNNNNNN NNNNNNNNNN NNNNNNNNNN
7651 NNNNNNNNNN NNNNNNNNNN NNNNNNNNNN NNNNNNNNNN NNNNNNNNNN
7701 NNNNNNNNNN NNNNNNNNNN NNNNNNNNNN NNNNNNNNNN NNNNNNNNNN
7751 NNNNNNNNNN NNNNNNNNNN NNNNNNNNNN NNNNNNNNNN NNNNNNNNNN
7801 NNNNNNNNNN NNNNNNNNNN NNNNNNNNNN NNNNNNNNNN NNNNNNNNNN
7851 NNNNNNNNNN NNNNNNNNNN NNNNNNNNNN NNNNNNNNNN NNNNNNNNNN
7901 NNNNNNNNNN NNNNNNNNNN NNNNNNNNNN NNNNNNNNNN NNNNNNNNNN
7951 NNNNNNNNNN NNNNNNNNNN NNNNNNNNNN NNNNNNNNNN NNNNNNNNNN
8001 NNNNNNNNNN NNNNNNNNNN NNNNNNNNNN NNNNNNNNNN NNNNNNNNNN
8051 NNNNNNNNNN NNNNNNNNNN NNNNNNNNNN NNNNNNNNNN NNNNNNNNNN
8101 NNNNNNNNNN NNNNNNNNNN NNNNNNNNNN NNNNNNNNNN NNNNNNNNNN
8151 NNNNNNNNNN NNNNNNNNNN NNNNNNNNNN NNNNNNNNNN NNNNNNNNNN
8201 NNNNNNNNNN NNNNNNNNNN NNNNNNNNNN NNNNNNNNNN NNNNNNNNNN
8251 NNNNNNNNNN NNNNNNNNNN NNNNNNNNNN NNNNNNNNNN NNNNNNNNNN
8301 NNNNNNNNNN NNNNNNNNNN NNNNNNNNNN NNNNNNNNNN NNNNNNNNNN
8351 NNNNNNNNNN NNNNNNNNNN NNNNNNNNNN NNNNNNNNNN NNNNNNNNNN
8401 NNNNNNNNNN NNNNNNNNNN NNNNNNNNNN NNNNNNNNNN NNNNNNNNNN
8451 NNNNNNNNNN NNNNNNNNNN NNNNNNNNNN NNNNNNNNNN NNNNNNNNNN
8501 NNNNNNNNNN NNNNNNNNNN NNNNNNNNNN NNNNNNNNNN NNNNNNNNNN
8551 NNNNNNNNNN NNNNNNNNNN NNNNNNNNNN NNNNNNNNNN NNNNNNNNNN
8601 NNNNNNNNNN NNNNNNNNNN NNNNNNNNNN NNNNNNNNNN NNNNNNNNNN
8651 NNNNNNNNNN NNNNNNNNNN NNNNNNNNNN NNNNNNNNNN NNNNNNNNNN
8701 NNNNNNNNNN NNNNNNNNNN NNNNNNNNNN NNNNNNNNNN NNNNNNNNNN
8751 NNNNNNNNNN NNNNNNNNNN NNNNNNNNNN NNNNNNNNNN NNNNNNNNNN
8801 NNNNNNNNNN NNNNNNNNNN NNNNNNNNNN NNNNNNNNNN NNNNNNNNNN
8851 NNNNNNNNNN NNNNNNNNNN NNNNNNNNNN NNNNNNNNNN NNNNNNNNNN
8901 NNNNNNNNNN NNNNNNNNNN NNNNNNNNNN NNNNNNNNNN NNNNNNNNNN
8951 NNNNNNNNNN NNNNNNNNNN NNNNNNNNNN NNNNNNNNNN NNNNNNNNNN
9001 NNNNNNNNNN NNNNNNNNNN NNNNNNNNNN NNNNNNNNNN NNNNNNNNNN
9051 NNNNNNNNNN NNNNNNNNNN NNNNNNNNNN NNNNNNNNNN NNNNNNNNNN
9101 NNNNNNNNNN NNNNNNNNNN NNNNNNNNNN NNNNNNNNNN NNNNNNNNNN
9151 NNNNNNNNNN NNNNNNNNNN NNNNNNNNNN NNNNNNNNNN NNNNNNNNNN
9201 NNNNNNNNNN NNNNNNNNNN NNNNNNNNNN NNNNNNNNNN NNNNNNNNNN
9251 NNNNNNNNNN NNNNNNNNNN NNNNNNNNNN NNNNNNNNNN NNNNNNNNNN
```

FIGURE 3C

```
9301 NNNNNNNNNN NNNNNNNNNN NNNNNNNNNN NNNNNNNNNN NNNNNNNNNN
9351 NNNNNNNNNN NNNNNNNNNN NNNNNNNNNN NNNNNNNNNN NNNNNNNNNN
9401 NNNNNNNNNN NNNNNNNNNN NNNNNNNNNN NNNNNNNNNN NNNNNNNNNN
9451 NNNNNNNNNN NNNNNNNNNN NNNNNNNNNN NNNNNNNNNN NNNNNNNNNN
9501 NNNNNNNNNN NNNNNNNNNN NNNNNNNNNN NNNNNNNNNN NNNNNNNNNN
9551 NNNNNNNNNN NNNNNNNNNN NNNNNNNNNN NNNNNNNNNN NNNNNNNNNN
9601 NNNNNNNNNN NNNNNNNNNN NNNNNNNNNN NNNNNNNNNN NNNNNNNNNN
9651 NNNNNNNNNN NNNNNNNNNN NNNNNNNNNN NNNNNNNNNN NNNNNNNNNN
9701 NNNNNNNNNN NNNNNNNNNN NNNNNNNNNN NNNNNNNNNN NNNNNNNNNN
9751 NNNNNNNNNN NNNNNNNNNN NNNNNNNNNN NNNNNNNNNN NNNNNNNNNN
9801 NNNNNNNNNN NNNNNNNNNN NNNNNNNNNN NNNNNNNNNN NNNNNNNNNN
9851 NNNNNNNNNN NNNNNNNNNN NNNNNNNNNN NNNNNNNNNN NNNNNNNNNN
9901 NNNNNNNNNN NNNNNNNNNN NNNNNNNNNN NNNNNNNNNN NNNNNNNNNN
9951 NNNNNNNNNN NNNNNNNNNN NNNNNNNNNN NNNNNNNNNN NNNNNNNNNN
10001 NNNNNNNNNN NNNNNNNNNN NNNNNNNNNN NNNNNNNNNN NNNNNNNNNN
10051 NNNNNNNNNN NNNNNNNNNN NNNNNNNNNN NNNNNNNNNN NNNNNNNNNN
10101 NNNNNNNNNN NNNNNNNNNN NNNNNNNNNN NNNNNNNNNN NNNNNNNNNN
10151 NNNNNNNNNN NNNNNNNNNN NNNNNNNNNN NNNNNNNNNN NNNNNNNNNN
10201 NNNNNNNNNN NNNNNNNNNN NNNNNNNNNN NNNNNNNNNN NNNNNNNNNN
10251 NNNNNNNNNN NNNNNNNNNN NNNNNNNNNN NNNNNNNNNN NNNNNNNNNN
10301 NNNNNNNNNN NNNNNNNNNN NNNNNNNNNN NNNNNNNNNN NNNNNNNNNN
10351 NNNNNNNNNN NNNNNNNNNN NNNNNNNNNN NNNNNNNNNN NNNNNNNNNN
10401 NNNNNNNNNN NNNNNNNNNN NNNNNNNNNN NNNNNNNNNN NNNNNNNNNN
10451 NNNNNNNNNN NNNNNNNNNN NNNNNNNNNN NNNNNNNNNN NNNNNNNNNN
10501 NNNNNNNNNN NNNNNNNNNN NNNNNNNNNN NNNNNNNNNN NNNNNNNNNN
10551 NNNNNNNNNN NNNNNNNNNN NNNNNNNNNN NNNNNNNNNN NNNNNNNNNN
10601 NNNNNNNNNN NNNNNNNNNN NNNNNNNNNN NNNNNNNNNN NNNNNNNNNN
10651 NNNNNNNNNN NNNNNNNNNN NNNNNNNNNN NNNNNNNNNN NNNNNNNNNN
10701 NNNNNNNNNN NNNNNNNNNN NNNNNNNNNN NNNNNNNNNN NNNNNNNNNN
10751 NNNNNNNNNN NNNNNNNNNN NNNNNNNNNN NNNNNNNNNN NNNNNNNNNN
10801 NNNNNNNNNN NNNNNNNNNN NNNNNNNNNN NNNNNNNNNN NNNNNNNNNN
10851 NNNNNNNNNN NNNNNNNNNN NNNNNNNNNN NNNNNNNNNN NNNNNNNNNN
10901 NNNNNNNNNN NNNNNNNNNN NNNNNNNNNN NNNNNNNNNN NNNNNNNNNN
10951 NNNNNNNNNN NNNNNNNNNN NNNNNNNNNN NNNNNNNNNN NNNNNNNNNN
11001 NNNNNNNNNN NNNNNNNNNN NNNNNNNNNN NNNNNNNNNN NNNNNNNNNN
11051 NNNNNNNNNN NNNNNNNNNN NNNNNNNNNN NNNNNNNNNN NNNNNNNNNN
11101 NNNNNNNNNN NNNNNNNNNN NNNNNNNNNN NNNNNNNNNN NNNNNNNNNN
11151 NNNNNNNNNN NNNNNNNNNN NNNNNNNNNN NNNNNNNNNN NNNNNNNNNN
11201 NNNNNNNNNN NNNNNNNNNN NNNNNNNNNN NNNNNNNNNN NNNNNNNNNN
11251 NNNNNNNNNN NNNNNNNNNN NNNNNNNNNN NNNNNNNNNN NNNNNNNNNN
11301 NNNNNNNNNN NNNNNNNNNN NNNNNNNNNN NNNNNNNNNN NNNNNNNNNN
11351 NNNNNNNNNN NNNNNNNNNN NNNNNNNNNN NNNNNNNNNN NNNNNNNNNN
11401 NNNNNNNNNN NNNNNNNNNN NNNNNNNNNN NNNNNNNNAG TTCCAGGCCC
11451 ACCCTTGGGC CAAACATGTT GAAGACCGCC ATGCTGTAGC TAGAACTTAC
11501 AAAAGATGTA AGCCTGGGCA TAGGTGGCCG GGTGCCGTTG TGGTCGCCAC
11551 GCTATCTTGG GGAGGGATTA AGGGCAAGGA AAATTCACCT TGAGGCCCAA
11601 GGAAGGCACA AGGGTTATCA CGTGAAGCCG AGGATCACCA TCACCATGCA
11651 CTAACACGCC TTGGGCAAGC ACGAAGCGAG GAGTTGCCAT CTCAAAACAA
11701 AAACGAAAAA CAAACAAACA AAATGCTAAT CAACTGTCAT TGGTAAGGCT
11751 TCTGGTCAAC AGTATGCTGT CAATAGTTAA GTTTTTGGGC TGGGCGCAGT
11801 GGCTCACGCC TGTAATCCCA GCACTTTGGG AGGCCAAAGC GGGTAGATCA
11851 CCTGAGGTCA GGAGTCGAGA CTAGCCTGGC AACATGGCG AAACCCAGTC
11901 TCTACTAAAA ATATAAAAAT TAGCCAGGCG TGGTGGTGGG CACTTGTAAT
11951 CCCAGCTACT CAGGAAGCTG AGGCAGAACT GCTTGAACTG GGAAGTGGAG
12001 GTTGCAGTGA GCCGAGATCG TGCCATTGCA TTCCAGCCTG GGCGACAAGA
12051 GCAAAACTCC ATCTCAAAAA AAAAAAAAAA AAAAAAGTT GTTTTTGGGG
12101 AGTCAAAAAT GAGGCCAGGC GCAGTGGCTC ATGCCTGTAA TCACAGCACT
12151 TTGGGAGGCC GAGGCGGGTG GATCACCTGA GGTCAGGAGT TCGTGACCAG
12201 CTTGGCCAAC CTGGTGAAAC CCCGTCTCTA CTAAAAATAC AAAAATTAGC
12251 CGGGCATGGT GGCGGGCGCC CGTAATCTCA GCTACTTGGG CGGCTGAGGC
12301 AGGAGAATTG CTTCAACCCG GGAGGCAGAG GTTGCAATGA GCTGAGATCG
12351 CGCCACTGCA CTCCAGCCTT GGCGACAGAG GGAGACTCCA TGTCAAATTA
```

FIGURE 3D

```
12401 AAAAAAAGAC CCCAGGATTT TGGACTGTGC AGGGGTCGGT GCCCCAAACC
12451 CCCACGTTGT TCAAGGTCAA CTGTACACTG TCATAGTCGG GAAAACTTCA
12501 TCACTGCAGC TGCTCCTGTT TCTTGAAACC TGAAGCGGGA AACTGGATCC
12551 TGGGACACTA CTGCCCCCTA TCGCCTGTTG GTCTTCAAAG AAATAATCCC
12601 TTCAATTTTG CAAGGCCTGT GGTGTCATTC CCTTTTAACA GATAAGGAAA
12651 CCGAGGCCAG GACGTGGTGG AAAATAATCA AGGTCACACA TCTATGTGCA
12701 AAAGTGGAGT AACAACCCAG GCTCCTCATT CCCAGGTCAG TCCAGTGACC
12751 TCAATTGACA TGAAATGTGT GAGGTCCTTC TGTGGCCCTG TGGCAGGGCC
12801 TGAAGAGGAC AGCGTATGTA AATCAAGTCT TGTGCCTTCA TGAGTGAGGC
12851 AGAGTAGAAA ATAACAGTAA TTCACTAGGA CCGAATCTGC ATTGTAAACA
12901 GAGAGGAAAG GGCTAGTATT TGGCAGAAGG ATGTCAAGGA ACATTTTAGA
12951 GATAAGAGGT GACATTTGGG TTCTGAGGGA TGAGTAGGAG TGTGCCAGGG
13001 TGCAAAGGAT GAAAAGACAG CTCTAGCAGC TGGTAAGGGC TAAGGGGCAT
13051 GGAGAAACAG CAAGACTTTG GGAACTGGT AGAATTCTAA TTCTGGAAAA
13101 TTTGAACAAG GTAATTTTTT GTGTGTGGTT AAGGTATTAC ATACATACAG
13151 TAAAATAAAA TGCAATAGTT GCTGGGTGTG GAGGCTCACG CCTGTTAATC
13201 CCAGTACTTT GGAAGGCAGA GGCGGGTGGA TCATCTGAAG GTCAGGAGTT
13251 CGAGACCAGC CTGACCAACA TGGTGAAAAC CCGTCTCTAC TAAAAATACA
13301 AAAATTACCT GGGTGTGGTG GCAGGCGCCC GTAATCCCAG CTACTTGGGA
13351 GGCTAAGGGA GAAGAATAGC TTGAAACCCG GAGGTGGAGG TTGCAGTGAG
13401 CTGAGATTGC ACTATTGCGC TCCAGCCTGG GTGACAAGAG TGAAAAGCTG
13451 TCTCAAAATA AAATAAAAAT GTAATAGTCT AATTGATTTT TTTAAAAAAT
13501 GTAGACATCC ACGTATCTAC CACCTAGGTA AAGATACTAG AGATTCCAGC
13551 AACCTGGGAG GATCCCTCGT GCCCCTTTCA GGTCTATATG AGCCTCCACC
13601 GTTCCCCAGT CCCCTGGAAG GAGAGGGGGT GGGAGAGGCA ACATGAAACC
13651 TAAAAACCAG TGGGCTTCGC GCCTGTAATC CCAGCTATTG GGTTGGCTGA
13701 GGCAGGAGGA TCACTTGCCC AGGAGTTGGA GGCTGCAGTG AGCTATGATC
13751 GCGCCACCGC ACTCCAGCCT GGGCGACAGA TCAAGACCCC ATCTCTAAGC
13801 AAACAAACAA ATAAACACCC CTCAAAACCC ATGGCTTCAG GCCTGGCGCG
13851 GTAGCTTACT TCTGTAATCT CAGCACTTTG GGAGGCCGAG GAGGGCGGAT
13901 CACTTGAGGT CAGGAGTTCC AGACCAGACT GGCCAACATG GCGAAACCCC
13951 GTCTCTACTA AAAATAAAA AAAAAAAAA ATTGGCCGGG CGCGGTGGCT
14001 CACACCTGTA ATTACCAGCA GNNNNNNNNN NNNNNNNNNN NNNNNNNNNN
14051 NNNNNNNNNN NNNNNNNNNN NTTTTAAAGA ATGTAGACAT CCACGTATCT
14101 ACCACCTAGG TAGAGATACT AGAGATTCCA GCAACCTGGG AGGATCCCTC
14151 GTGCGCCTTT CAGGTCTATA TGAGCCTCCA CCGTTCCCCA GTCCCCTGGA
14201 AGGAGAGGGG GTGGGAGAGG CAACATGAAA CCTAAAAACC AGTGGGCTTC
14251 GCGCCTGTAA TCCCAGCTAT TGGGTTGGCT GAGGCAGGAG GATCACTTGC
14301 CCAGGAGTTG GAGGCTGCAG TGAGCTATGA TCGCGCCACC GCACTCCAGC
14351 CTGGGCGACA GATCAAGACC CCATCTCTAA GCAAACAAAC AAATAAACAC
14401 CCCTCAAAAC CCATGGCTTC AGGCCTGGCG CGGTAGCTTA CTTCTGTAAT
14451 CTCAGCACTT TGGGAGGTCA AGGTGGGCGG ATCACTTGAA GTAAGGAGTT
14501 CAAGTACCAT CCTGGCTAAC ACGGTGAAAC CCCGTCTCTA CTGAAAAGAC
14551 AAAAAATTTA GCCGGGCGTG GTGGCGGGCG CCTTTAGTCT CAGCTACTCG
14601 GGAGGCTGAG GCAGGAGAAT GGCGTGAACC CGGGAGGTGG AGCTTGCAGT
14651 GAGCTGAGAT CGCACCACTG CACTCCAGTC TGGGTGACAG AGTGAGACTC
14701 CATCTCAAAA AAAAAAAAAA AGAAGTCAAA GTAGTAGAAA CTGCTGATAG
14751 ACTGAATGTG GGGGGTTAGG GAGATGGAGG AAGCTGAGTG ACTCCCAGGT
14801 TTCTTGCATG GGGGACTGAC TGGATATAAA ATTAGTTGTG GGCCGGGCAC
14851 GGTGGCTCAT GCCTTTAATC CCAGCACTTT GGGAGGCCAA AGCGGGCAGA
14901 TCACTTGAGC TCAGGAGTTC AAGACCAGCC TGGGAAACAT GGTGAGACCC
14951 CTTCTGTAAG GGNNNNNNNN NNNNNNNNNN NNNNNNNNNN NNNNNNNNNN
15001 NNNNNNNNNN NNNTGACCTT TTTTTGGCTC TGNTCGGTCA CTAGCANGCA
15051 AGTTATTGGG AGTCTACAAG ATTCTTTCAC ACTATGCCCT CAAAATTGAC
15101 TGTTCATGTA TGTGCAGACA TATAGAAAAA CAACGGGAGC CAGGCGCGGT
15151 GGCTCACGCC GGTAATCCCA GCACTTTGGG AGGCCAAGGC GGGTGAATCA
15201 TGGGGTCAGG AGTTCGAGAC CAGCCTGGCC AACATGGTGA AACCTGGTCT
15251 CTACTAAAAA TACAAAAAAT TAGCCGGGCG TGGTGGCGGG TGTCTGTAAT
15301 CCCAGCTACT TGGGAGGCTG AGGCAGGAGA ATCACTTGAA CCCAGGAGGC
15351 GGAGGTTGCA GTGAGCCGAG ATCGCGCCAG TGCACTCCAG CCTGGGCGAC
15401 AGAGCAAAAC TCTGTCTCAA AAAAAAAAAA AAAAAAAAGA AAAGAAAAGA
15451 AAAACAACTG GATGTAAATT GATGAACAAA TGAAGTAGTG CTGCTTTGGG
```

FIGURE 3E

```
15501 CAGTGGGATT ATAAGAGTCC TTTAAAGTTG TCTATGTGTT TATGTTTAAC
15551 TATATAACTA GAAGAAATAT TTATTTATTA GGATATGATA ATGGATGTGC
15601 TTAAAGTATT ACCTGTAAGG ATGTTTATGG TTTTTATGGC AATGTTGTTT
15651 ATAATAGCAG AAAATGAGAA CAGGTTAAAT GTCCAACTAT AGGGTAAAGG
15701 AAAAATAAAT TGTGGTTAGG ATGGGTTGTG AGGATCCTTA AATGGCTGAT
15751 ATATCTTTCA GCAAAAAAAG TAGGTTACAA AAAATATATA CCCTATACAA
15801 CATAATTCCA TATTTTATAT GCATATCAGG GGAGGGAAAA ACTCTAGAAG
15851 TGGGTAATCA AAATGTTAAA AGAACTTATC TATGAATGAG TGCTTTATAA
15901 CTGGTCTGTT CTTCAATTCT CAATTTTCCA AATTTTCTGT GAATGTCCTC
15951 TTTTCATAAT CAGATAAAAA TCATTGCACT AGGCTGGGCG TGGTGGTTCA
16001 CGCTTGTAAT CCCAGCACTT TGGGAGGCTG AGGCGGGTGG ATCACGTGGT
16051 CAGGAGTTCA AGACCAACCT GGCCAAGATG GTGAAACCCC AGCTCTACTA
16101 AAAATACAAA AATTACCCGG GCATGATGGC GGGAGCCTGT AATCCTAGCT
16151 ACTTGGGAGG CTGAGGCAGG AGAATCGCTT GAACTCGGGA GGCGGAGGTT
16201 GCAGTGAGCC GAGATTGCGC CACTGCACTC CATCCTAGGT AACACAGCCA
16251 GACTCTGTCT CAAAAAAAAA AAAAAATCAT TGCACTATAT TAAATTATAA
16301 TATAATTTGA TGAACTTATT GTCAATTAAA ATGTGTACTT AATTAAGAAA
16351 AAAGCCAGCC ACAATCCCAG TACCTTTACA AATGGTGTTT CCTTCTCATC
16401 GTCTCCAGGT GCTCAGCCGT ATTTCTTTAG TCTAGACGTT CCCATTTCCC
16451 CTGGGTGGAC AGGGATGGGG CACCAAGGGT GGATGGGTGG GGCAGGGATG
16501 CATTCAGTGC AGGGGAAGGC TGACTTTACC TCCTCCCTCC CAGGCAGAGG
16551 GGATGATCAG CGAAATCCGG ACCGCATTTG AGGAGGCCCT GGGACAGCTG
16601 GTTTGGATGG ATGAGAAGAC CCGCCAGGCA GCCAAGGAGA AAGTGAGCGG
16651 TGGCTAGGGT TGGGGCGCCA TCTTGAGGTG GGGTTCAAGG ATACAGTTTT
16701 GCTAGGAACC TGGGGAAGGA AACAAACCCT TAACCTGGTC TCTTCAGGCA
16751 GATGCCATCT ATGATATGAT TGGTTTCCCA GACTTTATCC TGGAGCCCAA
16801 AGAGCTGGAT GATGTTTATG ACGGGGTGAG TACCTACGCT CATCAGTACT
16851 GAACTTCAGC CCTGTAGAGG GCACTGTTCC CTGGGCTTAG AAATTGGGGC
16901 TCAAGCACTG GGAAAGAGGT GCTTGTCGGT TTCTTTTAGA GGCAGATGGA
16951 GGTAACCAGC ATTGTTAAAA TGTTGGCTCT GTGACAGGCT GCAGGCCAAA
17001 CAGCAGTGAA ATATAGTGCT AACGAGCCAA GATTTGGAGT CAAGCCTAAT
17051 CAAATTCTGT TTCTACCTCT AACTTGTAA CCTTAACAAA ATCTCTCTAG
17101 GCCTTGGTTT CATTTTCTGT AAAATGGGGG TCCTACTAGT GCCTTCCTCA
17151 TAGGGTTGTT GTGAGATAAA TGAATACAGT ATGTAAAAAA ACAGCACCCA
17201 TAACATAAAT GGCCTTTAAA TATTGCCAAT TATGGTTTAC TAGATATTTT
17251 ACAGTTGAGG AAACTGAGGT TTGGAGAGAT ACTAATGAGT AGCCAAACTG
17301 GCGCTATTAT CTTCTCCAAT GGATTCTCTT GCTCTCTGTC TACTTCCCAA
17351 CTTACCACAG AACAAANNNN NNNNNNNNNN NNNNNNNNNN NNNNNNNNNN
17401 NNNNNNNNNN NNNNNNNNNN NNNNNNNNNN NNNNNNNNNN NNNNNNNNNN
17451 NNNNNNNNNN NNNNNNNNNN NNNNNNNNNN NNNNNNNNNN NNNNNNNNNN
17501 NNNNNNNNNN NNNNNNNNNN NNNNNNNNNN NNNNNNNNNN NNNNNNNNNN
17551 NNNNNNNNNN NNNNNNNNNN NNNNNNNNNN NNNNNNNNNN NNNNNNNNNN
17601 NNNNNNNNNN NNNNNNNNNN NNNNNNNNNN NNNNNNNNNN NNNNNNNNNN
17651 NNNNNNNNNN NNNNNNNNNN NNNNNNNNNN NNNNNNNNNN NNNNNNNNNN
17701 NNNNNNNNNN NNNNNNNNNN NNNNNNNNNN NNNNNNNNNN NNNNNNNNNN
17751 NNNNNNNNNN NNNNNNNNNN NNNNNNNNNN NNNNNNNNNN NNNNNNNNNN
17801 NNNNNNNNNN NNNNNNNNNN NNNNNNNNNN NNNNNNNNNN NNNNNNNNNN
17851 NNNNNNNNNN NNNNNNNNNN NNNNNNNNNN NNNNNNNNNN NNNNNNNNNN
17901 NNNNNNNNNN NNNNNNNNNN NNNNNNNNNN NNNNNNNNNN NNNNNNNNNN
17951 NNNNNNNNNN NNNNNNNNNN NNNNNNNNNN NNNNNNNNNN NNNNNNNNNN
18001 NNNNNNNNNN NNNNNNNNNN NNNNNNNNNN NNNNNNNNNN NNNNNNNNNN
18051 NNNNNNNNNN NNNNNNNNNN NNNNNNNNNN NNNNNNNNNN NNNNNNNNNN
18101 NNNNNNNNNN NNNNNNNNNN NNNNNNNNNN NNNNNNNNNN NNNNNNNNNN
18151 NNNNNNNNNN NNNNNNNNNN NNNNNNNNNN NNNNNNNNNN NNNNNNNNNN
18201 NNNNNNNNNN NNNNNNNNNN NNNNNNNNNN NNNNNNNNNN NNNNNNNNNN
18251 NNNNNNNNNN NNNNNNNNNN NNNNNNNNNN NNNNNNNNNN NNNNNNNNNN
18301 NNNNNNNNNN NNNNNNNNNN NNNNNNNNNN NNNNNNNNNN NNNNNNNNNN
18351 NNNNNNNNNN NNNNNNNNNN NNNNNNNNNN NNNNNNNNNN NNNNNNNNNN
18401 NNNNNNNNNN NNNNNNNNNN NNNNNNNNNN NNNNNNNNNN NNNNNNNNNN
18451 NNNNNNNNNN NNNNNNNNNN NNNNNNNNNN NNNNNNNNNN NNNNNNNNNN
18501 NNNNNNNNNN NNNNNNNNNN NNNNNNNNNN NNNNNNNNNN NNNNNNNNNN
18551 NNNNNNNNNN NNNNNNNNNN NNNNNNNNNN NNNNNNNNNN NNNNNNNNNN
```

FIGURE 3F

```
18601  NNNNNNNNNN NNNNNNNNNN NNNNNNNNNN NNNNNNNNNN NNNNNNNNNN
18651  NNNNNNNNNN NNNNNNNNNN NNNNNNNNNN NNNNNNNNNN NNNNNNNNNN
18701  NNNNNNNNNN NNNNNNNNNN NNNNNNNNNN NNNNNNNNNN NNNNNNNNNN
18751  NNNNNNNNNN NNNNNNNNNN NNNNNNNNNN NNNNNNNNNN NNNNNNNNNN
18801  NNNNNNNNNN NNNNNNNNNN NNNNNAGAAT CACCAACAGC ATTGGATGAA
18851  AATAAAGAAG AACAAGAGGT TCGTTTGAGA GGAAGCCGGG AAAATTCTCT
18901  CGATAAAGAA ATGCAAGTGC GCGCGCGGCG CAACCACTAC AATAGTGTGT
18951  CGTCCACCCC AGAGAGTGAA GGGGGCCCCC CCCGCCCCAA AGGAAAGGGG
19001  TAGTGTCCAC GCCGCTCCAC AAAGAGAGAG AAGGAAAGAA GTAGTTTTCC
19051  CCCCCCCGGG GAGAAACCTT GGATGGGGCT CANCCCCCCC TCTTTTTTTT
19101  TCCCGCGAAA ACCCCCCCCA AAAAGTTTTT TTTAAAAAAC AAAAAAGGGG
19151  GGTTTGGTTT TTTGGGCCCC GTGGCCCCTT TGGTTTAAAT TGGGAGAAAG
19201  AGGGCTTAAA GGGGGGATTC AAGAAAAAAC CCCCCCCCAA TTGCCCCAAA
19251  TTGTAATTTC CTAACCCCAA AAGGGGCCCC TAAAATTTCC GGGGAAACCC
19301  GTGTGGGCAA TGGCCCATTA GTTTACCCAA TGCCTTTATT GACAAAGGTA
19351  GGGCCCCATG GAGTCGTCCC CTCTAGCCTA GAATTCCCAG TGGCTCCTGC
19401  AAGGGCCTTG GGACATTGAT GTAGCCCCAA GGGCCCTGAA GTCTGTGGAC
19451  CAGGGCTGGT GGGGCACTGC TGCCCCCAAG AGACGAGCTC TGGTTTTGGT
19501  GGGGTGCAAA GGTGAGTTCT CCTCAGGGCG CGAGTATGAC AAAGAAGGGA
19551  ACTGCGGCCC TGGTGGCAGA ATGAGTCCCT GGCAGCCTTC CGGAACCACA
19601  CGGCCTGCAT GGAGGAACAG TACAATCAAT ACCAGGTCAA TGGGGAGAGG    (SEQ ID NO:3)
```

FEATURES:
```
Start:    2113
Exon:     2113-2151
Intron:   2152-2439
Exon:     2440-2664
Intron:   2665-2850
Exon:     2851-2986
Intron:   2987-3209
Exon:     3210-3320
Intron:   3321-3519
Exon:     3520-3636
Intron:   3637-3853
Exon:     3854-3978
Intron:   3979-4095
Exon:     4096-4242
Intron:   4243-4420
Exon:     4421-4486
Intron:   4487-4576
Exon:     4577-4581
Intron:   4582-4707
Exon:     4708-4811
Intron:   4812-5525
Exon:     5526-5591
Intron:   5592-11594
Exon:     11595-11742
Intron:   11743-13150
Exon:     13151-13240
Intron:   13241-16408
Exon:     16409-16642
Intron:   16643-16747
Exon:     16748-16825
Intron:   16826-18962
Exon:     18963-19222
Intron:   19223-19321
Exon:     19322-19347
Intron:   19348-19526
Exon:     19527-19647
```

FIGURE 3G

CHROMOSOME MAP POSITION:
Chromosome # 3

ALLELIC VARIANTS (SNPs):

| DNA Position | Major | Minor | Domain | Protein Position | Major | Minor |
|---|---|---|---|---|---|---|
| 2707 | A | G | Intron | | | |
| 4209 | C | T | Exon | 289 | S | S |
| 4355 | - | T  G | Intron | | | |
| 15455 | - | A  C | Intron | | | |

Context:

DNA
Position
2707      TGACCTCGGTTGGCAACCCCGACTGTCTGGCAGATGGTGGAGTACAAACGGGCCACGCTT
          CGGGATGAAGACGCACCCGAGACCCCCGTAGAGGGCGGGGCCTCCCCGGACGCCATGGAG
          GTGGGCAAGGGGGCTTCCCCTTTCTCACCAGGCCCCAGCCCTGGCATGACGCCTGGCACA
          CCCAGGAGCTCTGGGCTGTTCTGGAGGGTCATCTGCCCCCACCTCCGCTCCATCTCTGGC
          CTCTGCTCTAGGACTATGGTGAGGCGATGCTAAGCCGTGACGTTGCACAAAACAGACTCA
          [A,G]
          GGCTCAACTCACTGGCTGGCCTCATTGCCCCCGGGCCCAGAGTTAACCCTGTGGCTCTGA
          AAACTGCCTGTGGCTTCACCCTCTGGTAATCTTGGATCCCTGCCCTGCATCTCAGTCACT
          CTCTGTCCCCTGTGTTCCCCAGGTGGGATTCCAGAAGGGGACAAGACAGCTGTTAGGCT
          CACGCACGCAGCTGGAGCTGGTCTTAGCAGGTGCCTCTCTACTGCTGGCTGCACTGCTTC
          TGGGCTGCCTTGTGGCCCTAGGGGTCCAGTACCACAGAGGTAGGTGGGCCCACACTCTTC 4209      CCTATCTTGCCTACAGGTGGAGCGCATTGAGGAGCTGGGAGCCCAGCCACTGAGAGACCT
          CATTGAGAAGGTAGGGCCACTGAGCCGGTTGAGGGCAGGGGAGCAGGAGAGGCCTTGAGA
          GAGGAGATGGCCCAGGAACGCTTTGGGAGCTCCTGCACTAATCATTCCACTTATGGTCTC
          TACATAGATTGGTGGTTGGAACATTACGGGGCCCTGGGACCAGGACAACTTTATGGAGGT
          GTTGAAGGCAGTAGCAGGGACCTACAGGGCCACCCCATTCTTCACCGTCTACATCAGTGC
          [C,T]
          GACTCTAAGAGTTCCAACAGCAATGTTATCCAGGTGATGAGCTGGGAAAGGGTGGGGAGA
          GACTTAGGGACACTTTGCTGAGCCCAGACTTCCCTCTCCTGTGACAGGCAGGCTGGGCTG
          ACCCCCCGGCCCCACCCCTACCCCCGCTCGGGAATTCAGGTTCCCATGGTGGGGAAAGCG
          AGGGGCTCACCTCCTTTCCTTGACATTGCAGGTGGACCAGTCTGGGCTCTTTCTGCCCTC
          TCGGGATTACTACTTAAACAGAACTGCCAATGAGAAAGTAAGGAACATCTTCCGAACCCC 4355      GAGCTCCTGCACTAATCATTCCACTTATGGTCTCTACATAGATTGGTGGTTGGAACATTA
          CGGGGCCCTGGGACCAGGACAACTTTATGGAGGTGTTGAAGGCAGTAGCAGGGACCTACA
          GGGCCACCCCATTCTTCACCGTCTACATCAGTGCCGACTCTAAGAGTTCCAACAGCAATG
          TTATCCAGGTGATGAGCTGGGAAAGGGTGGGGAGAGACTTAGGGACACTTTGCTGAGCCC
          AGACTTCCCTCTCCTGTGACAGGCAGGCTGGGCTGACCCCCCGGCCCCACCCCTACCCCC
          [-,T,G]
          CTCGGGAATTCAGGTTCCCATGGTGGGGAAAGCGAGGGGCTCACCTCCTTTCCTTGACAT
          TGCAGGTGGACCAGTCTGGGCTCTTTCTGCCCTCTCGGGATTACTACTTAAACAGAACTG
          CCAATGAGAAAGTAAGGAACATCTTCCGAACCCCCATCCCTACCCCTGGCTGAGCTGGGC
          TGATCCCTGTTGACTTTTCCCTTTGCCAAGGGTCAGAGCAGGGAAGGTGAGCCTATCCTG
          TCACCTAGTGAACAAACTGCCCCTCCTTTCTTTCTTCTTTTCTTCCTCCCTCCCTCCCTT 15455     CACGCCGGTAATCCCAGCACTTTGGGAGGCCAAGGCGGGTGAATCATGGGGTCAGGAGTT
          CGAGACCAGCCTGGCCAACATGGTGAAACCTGGTCTCTACTAAAAATACAAAAAATTAGC
          CGGGCGTGGTGGCGGGTGTCTGTAATCCCAGCTACTTGGGAGGCTGAGGCAGGAGAATCA
          CTTGAACCCAGGAGGCGGAGGTTGCAGTGAGCCGAGATCGCGCCAGTGCACTCCAGCCTG
          GGCGACAGAGCAAAACTCTGTCTCAAAAAAAAAAAAAAAAAAAGAAAAGAAAAGAAAAA
          [-,A,C]
          AACTGGATGTAAATTGATGAACAAATGAAGTAGTGCTGCTTTGGGCAGTGGGATTATAAG

FIGURE 3H

```
AGTCCTTTAAAGTTGTCTATGTGTTTATGTTTAACTATATAACTAGAAGAAATATTTATT
TATTAGGATATGATAATGGATGTGCTTAAAGTATTACCTGTAAGGATGTTTATGGTTTTT
ATGGCAATGTTGTTTATAATAGCAGAAAATGAGAACAGGTTAAATGTCCAACTATAGGGT
AAAGGAAAAATAAATTGTGGTTAGGATGGGTTGTGAGGATCCTTAAATGGCTGATATATC
```

FIGURE 3I

ISOLATED HUMAN ZINC METALLOPROTEASE PROTEINS

RELATED APPLICATIONS

The present application is a divisional of U.S. application Ser. No. 09/819,989, filed on Mar. 29, 2001, 2001 and issued on Nov. 19, 2002 as U.S. Pat. No. 6,482,629.

FIELD OF THE INVENTION

The present invention is in the field of enzyme proteins that are related to the metalloprotease enzyme subfamily, recombinant DNA molecules, and protein production. The present invention specifically provides novel peptides and proteins and nucleic acid molecules encoding such peptide and protein molecules, all of which are useful in the development of human therapeutics and diagnostic compositions and methods.

BACKGROUND OF THE INVENTION

Many human enzymes serve as targets for the action of pharmaceutically active compounds. Several classes of human enzymes that serve as such targets include helicase, steroid esterase and sulfatase, convertase, synthase, dehydrogenase, monoxygenase, transferase, kinase, glutanase, decarboxylase, isomerase and reductase. It is therefore important in developing new pharmaceutical compounds to identify target enzyme proteins that can be put into high-throughput screening formats. The present invention advances the state of the art by providing novel human drug target enzymes related to the metalloprotease subfamily.

Endothelin-Converting Enzymes

The novel human protein, and encoding gene, provided by the present invention is related to the family of metalloprotease enzymes (also referred to as the peptidase family M13, zinc metalloprotease family, and the neprilysin family) in general and shows a high degree of similarity to the endothelin-converting enzyme subfamily of metalloproteases. Furthermore, the protein of the present invention may be a novel isoform of the gene provided in Genbank gi7662200 (see the amino acid sequence alignment in FIG. 2).

Endothelin-coverting enzymes (ECE) are membrane-bound metalloproteases that catalyze the proteolytic activation of endothelins, which are potent vasoactive peptides. Endothelins are produced from biologically inactive intermediates known as big endothelins by ECE-catalyzed proteolytic processing. ECE function in secretory pathways as well as on the cell surface. ECE-1 and ECE-2 have been characterized. ECE-2 is structurally related to ECE-1, neural endopeptidase 24.11, and human Kell blood group protein. ECE-1 and ECE-2 are both inhibited by phosphoramidon. ECE-1 is most active at neutral pH, whereas an acidic pH is optimum for ECE-2. It is though that ECE-2 converts endogenously synthesized big endothelin-1 to mature endothelin-1 at the acidic environement of the trans-Golgi network (Emoto et al., *J. Biol Chem* 1995 June 23;270(25): 15262–8).

Metalloproteases

The metalloproteases may be one of the older classes of proteinases and are found in bacteria, fungi as well as in higher organisms. They differ widely in their sequences and their structures but the great majority of enzymes contain a zinc atom which is catalytically active. In some cases, zinc may be replaced by another metal such as cobalt or nickel without loss of the activity. Bacterial thermolysin has been well characterized and its crystallographic structure indicates that zinc is bound by two histidines and one glutamic acid. Many enzymes contain the sequence HEXXH, which provides two histidine ligands for the zinc whereas the third ligand is either a glutamic acid (thermolysin, neprilysin, alanyl aminopeptidase) or a histidine (astacin). Other families exhibit a distinct mode of binding of the Zn atom. The catalytic mechanism leads to the formation of a non covalent tetrahedral intermediate after the attack of a zinc-bound water molecule on the carbonyl group of the scissile bond. This intermediate is further decomposed by transfer of the glutamic acid proton to the leaving group.

Metalloproteases contain a catalytic zinc metal center which participates in the hydrolysis of the peptide backbone (reviewed in Power and Harper, in Protease Inhibitors, A. J. Barrett and G. Salversen (eds.) Elsevier, Amsterdam, 1986, p. 219). The active zinc center differentiates some of these proteases from calpains and trypsins whose activities are dependent upon the presence of calcium. Examples of metalloproteases include carboxypeptidase A, carboxypeptidase B, and thermolysin.

Metalloproteases have been isolated from a number of procaryotic and eucaryotic sources, e.g. Bacillus subtilis (McConn et al., 1964, J. Biol. Chem. 239:3706); Bacillus megaterium; Serratia (Miyata et al., 1971, Agr. Biol. Chem. 35:460); Clostridium bifennentans (MacFarlane et al., 1992, App. Environ. Microbiol. 58:1195–1200), Legionella pneumophila (Moffat et al., 1994, Infection and Immunity 62:751–3). In particular, acidic metalloproteases have been isolated from broad-banded copperhead venoms (Johnson and Ownby, 1993, Int. J. Biochem. 25:267–278), rattlesnake venoms (Chlou et al., 1992, Biochem. Biophys. Res. Commun. 187:389–396) and articular cartilage (Treadwell et al., 1986, Arch. Biochem. Biophys. 251:715–723). Neutral metalloproteases, specifically those having optimal activity at neutral pH have, for example, been isolated from Aspergillus sojae (Sekine, 1973, Agric. Biol. Chem. 37:1945–1952). Neutral metalloproteases obtained from Aspergillus have been classified into two groups, npI and npII (Sekine, 1972, Agric. Biol. Chem. 36:207–216). So far, success in obtaining amino acid sequence information from these fungal neutral metalloproteases has been limited. An npII metalloprotease isolated from Aspergillus oryzae has been cloned based on amino acid sequence presented in the literature (Tatsumi et al., 1991, Mol. Gen. Genet. 228:97–103). However, to date, no npI fungal metalloprotease has been cloned or sequenced. Alkaline metalloproteases, for example, have been isolated from Pseudomonas acruginosa (Baumann et al., 1993, EMBO J. 12:3357–3364) and the insect pathogen Xenorhabdus luminescens (Schmidt et al., 1998, Appl. Environ. Microbiol. 54:2793–2797).

Metalloproteases have been devided into several distinct families based primarily on activity and sturcture: 1) water nucleophile; water bound by single zinc ion ligated to two His (within the motif HEXXH) and Glu, His or Asp; 2) water nucleophile; water bound by single zinc ion ligated to His, Glu (within the motif HXXE) and His; 3) water nucleophile; water bound by single zinc ion ligated to His, Asp and His; 4) Water nucleophile; water bound by single zinc ion ligated to two His (within the motif HXXEH) and Glu and 5) water nucleophile; water bound by two zinc ions ligated by Lys, Asp, Asp, Asp, Glu.

Examples of members of the metalloproteinase family include, but are not limited to, membrane alanyl aminopeptidase (Homo sapiens), germinal peptidyl-dipeptidase A (*Homo sapiens*), thimet oligopeptidase (*Rattus norvegicus*), oligopeptidase F (*Lactococcus lactis*), mycolysin (*Streptomyces cacaoi*), immune inhibitor A (*Bacillus thuringiensis*), snapalysin (*Streptomyces lividans*), leishmanolysin (*Leishmania major*), microbial collagenase (*Vibrio alginolyticus*), microbial collagenase, class I (*Clostridium perfringens*), collagenase 1 (*Homo sapiens*), serralysin (*Serratia marcescens*), fragilysin (*Bacteroides fragilis*), gametolysin (*Chlamydomonas reinhardtii*), astacin (*Astacus fluviatilis*), adamalysin (*Crotalus adamanteus*), ADAM 10 (*Bos taurus*), neprilysin (*Homo sapiens*), carboxypeptidase A (*Homo sapiens*), carboxypeptidase E (*Bos taurus*), gamma-D-glutamyl-(L)-meso-diaminopimelate peptidase I (*Bacillus sphaericus*), vanY D-Ala-D-Ala carboxypeptidase (*Enterococcus faecium*), endolysin (bacteriophage A118), pitrilysin (*Escherichia coli*), mitochondrial processing peptidase (*Saccharomyces cerevisiae*), leucyl aminopeptidase (*Bos taurus*), aminopeptidase I (*Saccharomyces cerevisiae*), membrane dipeptidase (*Homo sapiens*), glutamate carboxypeptidase (Pseudomonas sp.), Gly-X carboxypeptidase (*Saccharomyces cerevisiae*), O-sialoglycoprotein endopeptidase (*Pasteurella haemolytica*), beta-lytic metalloendopeptidase (*Achromobacter lyticus*), methionyl aminopeptidase I (*Escherichia coli*), X-Pro aminopeptidase (*Escherichia coli*), X-His dipeptidase (*Escherichia coli*), IgA1-specific metalloendopeptidase (*Streptococcus sanguis*), tentoxilysin (*Clostridium tetani*), leucyl aminopeptidase (*Vibrio proteolyticus*), aminopeptidase (*Streptomyces griseus*), IAP aminopeptidase (*Escherichia coli*), aminopeptidase T (*Thermus aquaticus*), hyicolysin (*Staphylococcus hyicus*), carboxypeptidase Taq (*Thermus aquaticus*), anthrax lethal factor (*Bacillus anthracis*), penicillolysin (*Penicillium citrinum*), fungalysin (*Aspergillus fumigatus*), lysostaphin (*Staphylococcus simulans*), beta-aspartyl dipeptidase (*Escherichia coli*), carboxypeptidase Ss1 (*Sulfolobus solfataricus*), FtsH endopeptidase (*Escherichia coli*), glutamyl aminopeptidase (*Lactococcus lactis*), cytophagalysin (Cytophaga sp.), metalloendopeptidase (vaccinia virus), VanX D-Ala-D-Ala dipeptidase (*Enterococcus faecium*), Ste24p endopeptidase (*Saccharomyces cerevisiae*), dipeptidyl-peptidase III (*Rattus norvegicus*), S2P protease (*Homo sapiens*), sporulation factor SpoIVFB (*Bacillus subtilis*), and HYBD endopeptidase (*Escherichia coli*).

Metalloproteases have been found to have a number of uses. For example, there is strong evidence that a metalloprotease is involved in the in vivo proteolytic processing of the vasoconstrictor, endothelin-1. Rat metalloprotease has been found to be involved in peptide hormone processing. One important subfamily of the metalloproteases are the matrix metalloproteases.

A number of diseases are thought to be mediated by excess or undesired metalloprotease activity or by an imbalance in the ratio of the various members of the protease family of proteins. These include: a) osteoarthritis (Woessner, et al., J. Biol.Chem. 259(6), 3633, 1984; Phadke, et al., J. Rheumatol. 10, 852, 1983), b) rheumatoid arthritis (Mullins, et al., Biochim. Biophys. Acta 695, 117, 1983; Woolley, et al., Arthritis Rheum. 20, 1231, 1977; Gravallese, et al., Arthritis Rheum. 34, 1076, 1991), c) septic arthritis (Williams, et al., Arthritis Rheum. 33, 533, 1990), d) tumor metastasis (Reich, et al., Cancer Res. 48, 3307, 1988, and Matrisian, et al., Proc. Nat'l. Acad. Sci., USA 83, 9413, 1986), e) periodontal diseases (Overall, et al., J. Periodontal Res. 22, 81, 1987), f) corneal ulceration (Burns, et al., Invest. Opthalmol. Vis. Sci. 30, 1569, 1989), g) proteinuria (Baricos, et al., Biochem. J. 254, 609, 1988), h) coronary thrombosis from atherosclerotic plaque rupture (Henney, et al., Proc. Nat'l. Acad. Sci., USA 88, 8154–8158, 1991), i) aneurysmal aortic disease (Vine, et al., Clin. Sci. 81, 233, 1991), j) birth control (Woessner, et al., Steroids 54, 491, 1989), k) dystrophobic epidermolysis bullosa (Kronberger, et al., J. Invest. Dermatol. 79, 208, 1982), and l) degenerative cartilage loss following traumatic joint injury, m) conditions leading to inflammatory responses, osteopenias mediated by MMP activity, n) tempero mandibular joint disease, o) demyelating diseases of the nervous system (Chantry, et al., J. Neurochem. 50, 688, 1988).

Proteases and Cancer

Proteases are critical elements at several stages in the progression of metastatic cancer. In this process, the proteolytic degradation of structural protein in the basal membrane allows for expansion of a tumor in the primary site, evasion from this site as well as homing and invasion in distant, secondary sites. Also, tumor induced angiogenesis is required for tumor growth and is dependent on proteolytic tissue remodeling. Transfection experiments with various types of proteases have shown that the matrix metalloproteases play a dominant role in these processes in particular gelatinases A and B (MMP-2 and MMP-9, respectively). For an overview of this field see Mullins, et al., Biochim. Biophys. Acta 695, 177, 1983; Ray, et al., Eur. Respir. J. 7, 2062, 1994; Birkedal-Hansen, et al., Crit. Rev. Oral Biol. Med. 4, 197, 1993.

Furthermore, it was demonstrated that inhibition of degradation of extracellular matrix by the native matrix metalloprotease inhibitor TIMP-2 (a protein) arrests cancer growth (DeClerck, et al., Cancer Res. 52, 701, 1992) and that TIMP-2 inhibits tumor-induced angiogenesis in experimental systems (Moses, et al. Science 248, 1408, 1990). For a review, see DeClerck, et al., Ann. N. Y. Acad. Sci. 732, 222, 1994. It was further demonstrated that the synthetic matrix metalloprotease inhibitor batimastat when given intraperitoneally inhibits human colon tumor growth and spread in an orthotopic model in nude mice (Wang, et al. Cancer Res. 54, 4726, 1994) and prolongs the survival of mice bearing human ovarian carcinoma xenografts (Davies, et. al., Cancer Res. 53, 2087, 1993). The use of this and related compounds has been described in Brown, et al., WO-9321942 A2.

There are several patents and patent applications claiming the use of metalloprotease inhibitors for the retardation of metastatic cancer, promoting tumor regression, inhibiting cancer cell proliferation, slowing or preventing cartilage loss associated with osteoarthritis or for treatment of other diseases as noted above (e.g. Levy, et al., WO-9519965 A1; Beckett, et al., WO-9519956 A1; Beckett, et al., WO-9519957 A1;Beckett, et al., WO-9519961 A1;Brown, et al., WO-9321942 A2; Crimmin, et al., WO-9421625 A1; Dickens, et al., U.S. Pat. No. 4,599,361; Hughes, et al., U.S. Pat. No. 5,190,937; Broadhurst, et al., EP 574758 A1; Broadhurst, et al., EP 276436; and Myers, et al., EP 520573 A1.

Enzyme proteins, particularly members of the metalloprotease enzyme subfamily, are a major target for drug action and development. Accordingly, it is valuable to the field of pharmaceutical development to identify and characterize previously unknown members of this subfamily of enzyme proteins. The present invention advances the state of the art by providing previously unidentified human enzyme proteins, and the polynucleotides encoding them, that have homology to members of the metalloprotease enzyme subfamily. These novel compositions are useful in the diagnosis, prevention and treatment of biological processes associated with human diseases.

SUMMARY OF THE INVENTION

The present invention is based in part on the identification of amino acid sequences of human enzyme peptides and proteins that are related to the metalloprotease enzyme subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate enzyme activity in cells and tissues that express the enzyme. Experimental data as provided in FIG. 1 indicates expression in humans in the lung, amygdala, adrenal gland, hippocampus, and fetus.

DESCRIPTION OF THE FIGURE SHEETS

FIGS. 1A–1B provide the nucleotide sequence of a cDNA molecule that encodes the enzyme protein of the present invention. (SEQ ID NO: 1) In addition, structure and functional information is provided, such as ATG start, stop and tissue distribution, where available, that allows one to readily determine specific uses of inventions based on this molecular sequence. Experimental data as provided in FIG. 1 indicates expression in humans in the lung, amygdala, adrenal gland, hippocampus, and fetus.

FIGS. 2A–2D provide the predicted amino acid sequence of the enzyme of the present invention. (SEQ ID NO: 2) In addition structure and functional information such as protein family, function, and modification sites is provided where available, allowing one to readily determine specific uses of inventions based on this molecular sequence.

FIGS. 3A–3I provide genomic sequences that span the gene encoding the enzyme protein of the present invention. (SEQ ID NO: 3) In addition structure and functional information, such as intron/exon structure, promoter location, etc., is provided where available, allowing one to readily determine specific uses of inventions based on this molecular sequence. As illustrated in FIG. 3, SNPs were identified at 4 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a enzyme protein or part of a enzyme protein and are related to the metalloprotease enzyme subfamily. Utilizing these sequences, additional genomic sequences were assembled and transcript and/or cDNA sequences were isolated and characterized. Based on this analysis, the present invention provides amino acid sequences of human enzyme peptides and proteins that are related to the metalloprotease enzyme subfamily, nucleic acid sequences in the form of transcript sequences, cDNA sequences and/or genomic sequences that encode these enzyme peptides and proteins, nucleic acid variation (allelic information), tissue distribution of expression, and information about the closest art known protein/peptide/domain that has structural or sequence homology to the enzyme of the present invention.

In addition to being previously unknown, the peptides that are provided in the present invention are selected based on their ability to be used for the development of commercially important products and services. Specifically, the present peptides are selected based on homology and/or structural relatedness to known enzyme proteins of the metalloprotease enzyme subfamily and the expression pattern observed. Experimental data as provided in FIG. 1 indicates expression in humans in the lung, amygdala, adrenal gland, hippocampus, and fetus. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known metalloprotease family or subfamily of enzyme proteins.

Specific Embodiments

Peptide Molecules

The present invention provides nucleic acid sequences that encode protein molecules that have been identified as being members of the enzyme family of proteins and are related to the metalloprotease enzyme subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the enzyme peptides of the present invention, enzyme peptides, or peptides/proteins of the present invention.

The present invention provides isolated peptide and protein molecules that consist of, consist essentially of, or comprise the amino acid sequences of the enzyme peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the enzyme peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated enzyme peptide can be purified from cells that naturally express it, purified from cells that have been altered to express it (recombinant), or synthesized using known protein synthesis methods. Experimental data as provided in FIG. 1 indicates expression in humans in the lung, amygdala, adrenal gland, hippocampus, and fetus. For example, a nucleic acid molecule encoding the enzyme peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO: 2), for example, proteins encoded by the transcript/cDNA nucleic acid sequences shown in FIG. 1 (SEQ ID NO: 1) and the genomic sequences provided in FIG. 3 (SEQ ID NO: 3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO: 2), for example, proteins encoded by the transcript/cDNA nucleic acid sequences shown in FIG. 1 (SEQ ID NO: 1) and the genomic sequences provided in FIG. 3 (SEQ ID NO: 3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO: 2), for example, proteins encoded by the transcript/cDNA nucleic acid sequences shown in FIG. 1 (SEQ ID NO: 1) and the genomic sequences provided in FIG. 3 (SEQ ID NO: 3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the enzyme peptides of the present invention are the naturally occurring mature proteins. A brief description of how various types of these proteins can be made/isolated is provided below.

The enzyme peptides of the present invention can be attached to heterologous sequences to form chimeric or fusion proteins. Such chimeric and fusion proteins comprise a enzyme peptide operatively linked to a heterologous protein having an amino acid sequence not substantially homologous to the enzyme peptide. "Operatively linked" indicates that the enzyme peptide and the heterologous protein are fused in-frame. The heterologous protein can be fused to the N-terminus or C-terminus of the enzyme peptide.

In some uses, the fusion protein does not affect the activity of the enzyme peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant enzyme peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., Current Protocols in Molecular Biology, 1992). Moreover, many expression vectors are commercially available that already encode a fusion moiety (e.g., a GST protein). A enzyme peptide-encoding nucleic acid can be cloned into such an expression vector such that the fusion moiety is linked in-frame to the enzyme peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the enzyme peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology,* Lesk, A. M., ed., Oxford University Press, New York, 1988; *Biocomputing: Informatics and Genome Projects,* Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology,* von Heinje, G., Academic Press, 1987; and *Sequence Analysis Primer,* Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al, *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the enzyme peptides of the present invention as well as being encoded by the same genetic locus as the enzyme peptide provided herein. The gene encoding the novel enzyme of the present invention is located on a genome component that has been mapped to human chromosome 3 (as indicated in FIG. 3), which is supported by multiple lines of evidence, such as STS and BAC map data.

Allelic variants of a enzyme peptide can readily be identified as being a human protein having a high degree (significant) of sequence homology/identity to at least a portion of the enzyme peptide as well as being encoded by the same genetic locus as the enzyme peptide provided herein. Genetic locus can readily be determined based on the genomic information provided in FIG. 3, such as the genomic sequence mapped to the reference human. The gene encoding the novel enzyme of the present invention is located on a genome component that has been mapped to human chromosome 3 (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a enzyme peptide encoding nucleic acid molecule under stringent conditions as more fully described below.

FIG. 3 provides information on SNPs that have been found in the gene encoding the enzyme of the present invention. SNPs were identified at 4 different nucleotide positions. Some of these SNPs that are located outside the ORF and in introns may affect gene transcription.

Paralogs of a enzyme peptide can readily be identified as having some degree of significant sequence homology/identity to at least a portion of the enzyme peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a enzyme peptide encoding nucleic acid molecule under moderate to stringent conditions as more fully described below.

Orthologs of a enzyme peptide can readily be identified as having some degree of significant sequence homology/identity to at least a portion of the enzyme peptide as well as being encoded by a gene from another organism. Preferred orthologs will be isolated from mammals, preferably primates, for the development of human therapeutic targets and agents. Such orthologs will be encoded by a nucleic acid sequence that will hybridize to a enzyme peptide encoding nucleic acid molecule under moderate to stringent conditions, as more fully described below, depending on the degree of relatedness of the two organisms yielding the proteins.

Non-naturally occurring variants of the enzyme peptides of the present invention can readily be generated using recombinant techniques. Such variants include, but are not limited to deletions, additions and substitutions in the amino acid sequence of the enzyme peptide. For example, one class of substitutions are conserved amino acid substitution. Such substitutions are those that substitute a given amino acid in a enzyme peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant enzyme peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/ regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as enzyme activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the enzyme peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a enzyme peptide. Such fragments can be chosen based on the ability to retain one or more of the biological activities of the enzyme peptide or could be chosen for the ability to perform a fiction, e.g. bind a substrate or act as an immunogen. Particularly important fragments are biologically active fragments, peptides that are, for example, about 8 or more amino acids in length. Such fragments will typically comprise a domain or motif of the enzyme peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in enzyme peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N.Y Acad. Sci.* 663:48–62 (1992)).

Accordingly, the enzyme peptides of the present invention also encompass derivatives or analogs in which a substituted amino acid residue is not one encoded by the genetic code, in which a substituent group is included, in which the mature enzyme peptide is fused with another compound, such as a compound to increase the half-life of the enzyme peptide (for example, polyethylene glycol), or in which the additional amino acids are fused to the mature enzyme peptide, such as a leader or secretory sequence or a sequence for purification of the mature enzyme peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a enzyme-effector protein interaction or enzyme-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, enzymes isolated from humans and their human/mammalian orthologs serve as targets for identifying agents for use in mammalian therapeutic applications, e.g. a human drug, particularly in modulating a biological or pathological response in a cell or tissue that expresses the enzyme. Experimental data as provided in FIG. 1 indicates that the enzymes of the present invention are expressed in humans in the lung, amygdala, adrenal gland, and fetus, as indicated by virtual northern blot analysis. In addition, PCR-based tissue screening panels indicate expression in the hippocampus. A large percentage of pharmaceutical agents are being developed that modulate the activity of enzyme proteins, particularly members of the metalloprotease subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in the lung, amygdala, adrenal gland, hippocampus, and fetus. Such uses can readily be determined using the information provided herein, that which is known in the art, and routine experimentation.

The proteins of the present invention (including variants and fragments that may have been disclosed prior to the present invention) are useful for biological assays related to enzymes that are related to members of the metalloprotease subfamily. Such assays involve any of the known enzyme functions or activities or properties useful for diagnosis and treatment of enzyme-related conditions that are specific for the subfamily of enzymes that the one of the present invention belongs to, particularly in cells and tissues that express the enzyme. Experimental data as provided in FIG. 1 indicates that the enzymes of the present invention are expressed in humans in the lung, amygdala, adrenal gland, and fetus, as indicated by virtual northern blot analysis. In addition, PCR-based tissue screening panels indicate expression in the hippocampus.

The proteins of the present invention are also useful in drug screening assays, in cell-based or cell-free systems. Cell-based systems can be native, i.e., cells that normally express the enzyme, as a biopsy or expanded in cell culture. Experimental data as provided in FIG. 1 indicates expression in humans in the lung, amygdala, adrenal gland, hippocampus, and fetus. In an alternate embodiment, cell-based assays involve recombinant host cells expressing the enzyme protein.

The polypeptides can be used to identify compounds that modulate enzyme activity of the protein in its natural state or an altered form that causes a specific disease or pathology associated with the enzyme. Both the enzymes of the present invention and appropriate variants and fragments can be used in high-throughput screens to assay candidate compounds for the ability to bind to the enzyme. These compounds can be further screened against a functional enzyme to determine the effect of the compound on the enzyme activity. Further, these compounds can be tested in animal or invertebrate systems to determine activity/effectiveness. Compounds can be identified that activate (agonist) or inactivate (antagonist) the enzyme to a desired degree.

Further, the proteins of the present invention can be used to screen a compound for the ability to stimulate or inhibit interaction between the enzyme protein and a molecule that normally interacts with the enzyme protein, e.g. a substrate or a component of the signal pathway that the enzyme protein normally interacts (for example, another enzyme). Such assays typically include the steps of combining the enzyme protein with a candidate compound under conditions that allow the enzyme protein, or fragment, to interact with the target molecule, and to detect the formation of a complex between the protein and the target or to detect the biochemical consequence of the interaction with the enzyme protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant enzymes or appropriate fragments containing mutations that affect enzyme function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) enzyme activity. The assays typically involve an assay of events in the signal transduction pathway that indicate enzyme activity. Thus, the phosphorylation of a substrate, activation of a protein, a change in the expression of genes that are up- or down-regulated in response to the enzyme protein dependent signal cascade can be assayed.

Any of the biological or biochemical functions mediated by the enzyme can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the enzyme can be assayed. Experimental data as provided in FIG. 1 indicates that the enzymes of the present invention are expressed in humans in the lung, amygdala, adrenal gland, and fetus, as indicated by virtual northern blot analysis. In addition, PCR-based tissue screening panels indicate expression in the hippocampus.

Binding and/or activating compounds can also be screened by using chimeric enzyme proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native enzyme. Accordingly, a different set of signal transduction components is available as an end-point assay for activation. This allows for assays to be performed in other than the specific host cell from which the enzyme is derived.

The proteins of the present invention are also useful in competition binding assays in methods designed to discover compounds that interact with the enzyme (e.g. binding partners and/or ligands). Thus, a compound is exposed to a enzyme polypeptide under conditions that allow the compound to bind or to otherwise interact with the polypeptide. Soluble enzyme polypeptide is also added to the mixture. If the test compound interacts with the soluble enzyme polypeptide, it decreases the amount of complex formed or activity from the enzyme target. This type of assay is particularly useful in cases in which compounds are sought that interact with specific regions of the enzyme. Thus, the soluble polypeptide that competes with the target enzyme region is designed to contain peptide sequences corresponding to the region of interest.

To perform cell free drug screening assays, it is sometimes desirable to immobilize either the enzyme protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be,provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of enzyme-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a enzyme-binding protein and a candidate compound are incubated in the enzyme protein-presenting wells and the amount of complex trapped in the well can be quantitated. Methods for detecting such complexes, in addition to those described above for the GST-immobilized complexes, include immunodetection of complexes using antibodies reactive with the enzyme protein target molecule, or which are reactive with enzyme protein and compete with the target molecule, as well as enzyme-linked assays which rely on detecting an enzymatic activity associated with the target molecule.

Agents that modulate one of the enzymes of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of enzyme protein activity identified according to these drug screening assays can be used to treat a subject with a disorder mediated by the enzyme pathway, by treating cells or tissues that express the enzyme. Experimental data as provided in FIG. 1 indicates expression in humans in the lung, amygdala, adrenal gland, hippocampus, and fetus. These methods of treatment include the steps of administering a modulator of enzyme activity in a pharmaceutical composition to a subject in need of such treatment, the modulator being identified as described herein.

In yet another aspect of the invention, the enzyme proteins can be used as "bait proteins" in a two-hybrid assay or three-hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Biotechniques 14:920–924; Iwabuchi et al. (1993) Oncogene 8:1693–1696; and Brent WO94/10300), to identify other proteins, which bind to or interact with the enzyme and are involved in enzyme activity. Such enzyme-binding proteins are also likely to be involved in the propagation of signals by the enzyme proteins or enzyme targets as, for example, downstream elements of a enzyme-mediated signaling pathway. Alternatively, such enzyme-binding proteins are likely to be enzyme inhibitors.

The two-hybrid system is based on the modular nature of most transcription factors, which consist of separable DNA-binding and activation domains. Briefly, the assay utilizes two different DNA constructs. In one construct, the gene that codes for a enzyme protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a enzyme-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the enzyme protein.

This invention further pertains to novel agents identified by the above-described screening assays. Accordingly, it is within the scope of this invention to further use an agent identified as described herein in an appropriate animal model. For example, an agent identified as described herein (e.g., a enzyme-modulating agent, an antisense enzyme nucleic acid molecule, a enzyme-specific antibody, or a enzyme-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The enzyme proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in the lung, amygdala, adrenal gland, hippocampus, and fetus. The method involves contacting a biological sample with a compound capable of interacting with the enzyme protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered enzyme activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the enzyme protein in which one or more of the enzyme functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and enzyme activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in the lung, amygdala, adrenal gland, hippocampus, and fetus. Accordingly, methods for treatment include the use of the enzyme protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the enzyme proteins. Antibodies can be prepared from any region of the peptide as described herein. However, preferred regions will include those involved in function/activity and/or enzyme/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that the enzymes of the present invention are expressed in humans in the lung, amygdala, adrenal gland, and fetus, as indicated by virtual northern blot analysis. In addition, PCR-based tissue screening panels indicate expression in the hippocampus. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in the lung, amygdala, adrenal gland, hippocampus, and fetus. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in the lung, amygdala, adrenal gland, hippocampus, and fetus. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in the lung, amygdala, adrenal gland, hippocampus, and fetus. Thus, where a specific protein has been correlated with expression in a specific tissue, antibodies that are specific for this protein can be used to identify a tissue type.

The antibodies are also useful for inhibiting protein function, for example, blocking the binding of the enzyme peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a enzyme peptide or protein of the present invention (cDNA, transcript and genomic sequence). Such nucleic acid molecules will consist of, consist essentially of, or comprise a nucleotide sequence that encodes one of the enzyme peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5KB, 4KB, 3KB, 2KB, or 1KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO: 1, transcript sequence and SEQ ID NO: 3, genomic sequence), or any nucleic acid molecule that encodes the protein provided in FIG. 2, SEQ ID NO: 2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO: 1, transcript sequence and SEQ ID NO: 3, genomic sequence), or any nucleic acid molecule that encodes the protein provided in FIG. 2, SEQ ID NO: 2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO: 1, transcript sequence and SEQ ID NO: 3, genomic sequence), or any nucleic acid molecule that encodes the protein provided in FIG. 2, SEQ ID NO: 2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the enzyme peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the enzyme proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments-include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. The gene encoding the novel enzyme of the present invention is located on a genome component that has been mapped to human chromosome 3 (as indicated in FIG. 3), which is supported by multiple lines of evidence, such as STS and BAC map data.

FIG. 3 provides information on SNPs that have been found in the gene encoding the enzyme of the present invention. SNPs were identified at 4 different nucleotide positions. Some of these SNPs that are located outside the ORF and in introns may affect gene transcription.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6× sodium chloride/sodium citrate (SSC) at about 45 C., followed by one or more washes in 0.2× SSC, 0.1% SDS at 50–65 C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at 4 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The gene encoding the novel enzyme of the present invention is located on a genome component that has been mapped to human chromosome 3 (as indicated in FIG. 3), which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that the enzymes of the present invention are expressed in humans in the lung, amygdala, adrenal gland, and fetus, as indicated by virtual northern blot analysis. In addition, PCR-based tissue screening panels indicate expression in the hippocampus. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in enzyme protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a enzyme protein, such as by measuring a level of a enzyme-encoding nucleic acid in a sample of cells from a subject e.g., mRNA or genomic DNA, or determining if a enzyme gene has been mutated. Experimental data as provided in FIG. 1 indicates that the enzymes of the present invention are expressed in humans in the lung, amygdala, adrenal gland, and fetus, as indicated by virtual northern blot analysis. In addition, PCR-based tissue screening panels indicate expression in the hippocampus.

Nucleic acid expression assays are useful for drug screening to identify compounds that modulate enzyme nucleic acid expression.

The invention thus provides a method for identifying a compound that can be used to treat a disorder associated with nucleic acid expression of the enzyme gene, particularly biological and pathological processes that are mediated by the enzyme in cells and tissues that express it. Experimental data as provided in FIG. 1 indicates expression in humans in the lung, amygdala, adrenal gland, hippocampus, and fetus. The method typically includes assaying the ability of the compound to modulate the expression of the enzyme nucleic acid and thus identifying a compound that can be used to treat a disorder characterized by undesired enzyme nucleic acid expression. The assays can be performed in cell-based and cell-free systems. Cell-based assays include cells naturally expressing the enzyme nucleic acid or recombinant cells genetically engineered to express specific nucleic acid sequences.

The assay for enzyme nucleic acid expression can involve direct assay of nucleic acid levels, such as mRNA levels, or on collateral compounds involved in the signal pathway. Further, the expression of genes that are up- or down-regulated in response to the enzyme protein signal pathway can also be assayed. In this embodiment the regulatory regions of these genes can be operably linked to a reporter gene such as luciferase.

Thus, modulators of enzyme gene expression can be identified in a method wherein a cell is contacted with a candidate compound and the expression of mRNA determined. The level of expression of enzyme mRNA in the presence of the candidate compound is compared to the level of expression of enzyme mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate enzyme nucleic acid expression in cells and tissues that express the enzyme. Experimental data as provided in FIG. 1 indicates that the enzymes of the present invention are expressed in humans in the lung, amygdala, adrenal gland, and fetus, as indicated by virtual northern blot analysis. In addition, PCR-based tissue screening panels indicate expression in the hippocampus. Modulation includes both up-regulation (i.e. activation or agonization) or down-regulation (suppression or antagonization) or nucleic acid expression.

Alternatively, a modulator for enzyme nucleic acid expression can be a small molecule or drug identified using the screening assays described herein as long as the drug or small molecule inhibits the enzyme nucleic acid expression in the cells and tissues that express the protein. Experimental data as provided in FIG. 1 indicates expression in humans in the lung, amygdala, adrenal gland, hippocampus, and fetus.

The nucleic acid molecules are also useful for monitoring the effectiveness of modulating compounds on the expression or activity of the enzyme gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in enzyme nucleic acid expression, and particularly in qualitative changes that lead to pathology. The nucleic acid molecules can be used to detect mutations in enzyme genes and gene expression products such as mRNA. The nucleic acid molecules can be used as hybridization probes to detect naturally occurring genetic mutations in the enzyme gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the enzyme gene associated with a dysfunction provides a diagnostic tool for an active disease or susceptibility to disease when the disease results from overexpression, underexpression, or altered expression of a enzyme protein.

Individuals carrying mutations in the enzyme gene can be detected at the nucleic acid level by a variety of techniques. FIG. 3 provides information on SNPs that have been found in the gene encoding the enzyme of the present invention. SNPs were identified at 4 different nucleotide positions. Some of these SNPs that are located outside the ORF and in introns may affect gene transcription. The gene encoding the novel enzyme of the present invention is located on a genome component that has been mapped to human chromosome 3 (as indicated in FIG. 3), which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a enzyme gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method.

Furthermore, sequence differences between a mutant enzyme gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the enzyme gene in an individual in order to select an appropriate compound or dosage regimen for treatment. FIG. 3 provides information on SNPs that have been found in the gene encoding the enzyme of the present invention. SNPs were identified at 4 different nucleotide positions. Some of these SNPs that are located outside the ORF and in introns may affect gene transcription.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control enzyme gene expression in cells, tissues, and organisms. A DNA antisense nucleic acid molecule is designed to be complementary to a region of the gene involved in transcription, preventing transcription and hence production of enzyme protein. An antisense RNA or DNA nucleic acid molecule would hybridize to the mRNA and thus block translation of mRNA into enzyme protein.

Alternatively, a class of antisense molecules can be used to inactivate mRNA in order to decrease expression of enzyme nucleic acid. Accordingly, these molecules can treat a disorder characterized by abnormal or undesired enzyme nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the enzyme protein, such as substrate binding.

The nucleic acid molecules also provide vectors for gene therapy in patients containing cells that are aberrant in enzyme gene expression. Thus, recombinant cells, which include the patient's cells that have been engineered ex vivo and returned to the patient, are introduced into an individual where the cells produce the desired enzyme protein to treat the individual.

The invention also encompasses kits for detecting the presence of a enzyme nucleic acid in a biological sample. Experimental data as provided in FIG. 1 indicates that the enzymes of the present invention are expressed in humans in the lung, amygdala, adrenal gland, and fetus, as indicated by virtual northern blot analysis. In addition, PCR-based tissue screening panels indicate expression in the hippocampus. For example, the kit can comprise reagents such as a labeled or labelable nucleic acid or agent capable of detecting enzyme nucleic acid in a biological sample; means for determining the amount of enzyme nucleic acid in the sample; and means for comparing the amount of enzyme nucleic acid in the sample with a standard. The compound or agent can be packaged in a suitable container. The kit can further comprise instructions for using the kit to detect enzyme protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS: 1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application W095/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application W095/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the enzyme proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the enzyme gene of the present invention. FIG. 3 provides information on SNPs that have been found in the gene encoding the enzyme of the present invention. SNPs were identified at 4 different nucleotide positions. Some of these SNPs that are located outside the ORF and in introns may affect gene transcription.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques,* Elsevier Science Publishers, Amsterdam, The Netherlands (1986); Bullock, G. R. et al., *Techniques in Immunocytochemistry,* Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology,* Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified enzyme gene of the present invention can be routinely identified using the sequence information disclosed herein can be readily incorporated into one of the established kit formats which are well known in the art, particularly expression arrays.

Vectors/host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules.

Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from E. Coli, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual.* 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual.* 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, E. coli, Streptomyces, and *Salmonella typhimurium.* Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enteroenzyme. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion E. coli expression vectors include pTrc (Amann et al, *Gene* 69:301–315 (1988)) and pET 11d (Studier et al, *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990) 119–128). Alternatively, the sequence of the nucleic acid molecule of interest can be altered to provide preferential codon usage for a specific host cell, for example E. coli. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSecl (Baldari, et al, *EMBO J.* 6:229–234 (1987)), pMFa (Kujan et al, *Cell* 30:933–943(1982)), pJRY88 (Schultz et al, *Gene* 54:113–123 (1987)), and pYES2 (Invitrogen Corporation, San Diego, Calf.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al, *Mol. Cell Biol.* 3:2156–2165 (1983)) and the pVL series (Lucklow et al, *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed., Cold Spring Harbor Laboratory,* Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed., Cold Spring Harbor Laboratory,* Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as enzymes, appropriate secretion signals are incorporated into the vector. The signal sequence can be endogenous to the peptides or heterologous to these peptides.

Where the peptide is not secreted into the medium, which is typically the case with enzymes, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a enzyme protein or peptide that can be further purified to produce desired amounts of enzyme protein or fragments. Thus, host cells containing expression vectors are useful for peptide production.

Host cells are also useful for conducting cell-based assays involving the enzyme protein or enzyme protein fragments, such as those described above as well as other formats known in the art. Thus, a recombinant host cell expressing a native enzyme protein is useful for assaying compounds that stimulate or inhibit enzyme protein function.

Host cells are also useful for identifying enzyme protein mutants in which these functions are affected. If the mutants naturally occur and give rise to a pathology, host cells containing the mutations are useful to assay compounds that have a desired effect on the mutant enzyme protein (for example, stimulating or inhibiting function) which may not be indicated by their effect on the native enzyme protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a enzyme protein and identifying and evaluating modulators of enzyme protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the enzyme protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the enzyme protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO97/07668 and WO97/07669. In brief, a cell, e.g., a somatic cell, from the transgenic animal can be isolated and induced to exit the growth, cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, enzyme protein activation, and signal transduction, may not be evident from in vitro cell-free or cell-based assays. Accordingly, it is useful to provide non-human transgenic animals to assay in vivo enzyme protein function, including substrate interaction, the effect of specific mutant enzyme proteins on enzyme protein function and substrate interaction, and the effect of chimeric enzyme proteins. It is also possible to assess the effect of null mutations, that is, mutations that substantially or completely eliminate one or more enzyme protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated polypeptide having an amino acid sequence consisting of SEQ ID NO:2.
2. An isolated polypeptide having an amino acid sequence comprising SEQ ID NO:2.
3. A composition comprising the polypeptide of claim 1 and a carrier.
4. A composition comprising the polypeptide of claim 2 and a carrier.

* * * * *

SEQUENCE LISTING

<160> NUMBER OF SEQ ID NOS: 4

<210> SEQ ID NO 1
<211> LENGTH: 3377
<212> TYPE: DNA
<213> ORGANISM: Human

<400> SEQUENCE: 1

```
tcgcggcggc cgtgatggct ggtgacggcg gggccgggca ggggaccggg gccgcggccc      60
gggagcgggc cagctgccgg gagccctgaa tcaccgcctg gcccgactcc accatgaacg     120
tcgcgctgca ggagctggga gctggcagca acatggtgga gtacaaacgg gccacgcttc     180
gggatgaaga cgcacccgag accccgtag agggcgggc ctccccggac gccatggagg      240
tgggcaaggg ggcttcccct ttctcaccag gccccagccc tggcatgacg cctggcacac     300
ccaggagctc tgggctgttc tggagggtca cctgccccca cctccgctcc atctctggcc     360
```

-continued

```
tctgctctag gactatggtg ggattccaga aggggacaag acagctgtta ggctcacgca    420
cgcagctgga gctggtctta gcaggtgcct ctctactgct ggctgcactg cttctgggct    480
gccttgtggc cctagggtc cagtaccaca gagacccatc ccacagcacc tgccttacag     540
aggcctgcat tcgagtggct ggaaaaatcc tggagtccct ggaccgaggg gtgagcccct    600
gtgaggactt ttaccagttc tcctgtgggg gctggattcg gaggaacccc ctgcccgatg    660
ggcgttctcg ctggaacacc ttcaacagcc tctgggacca aaaccaggcc atactgaagc    720
acctgcttga aaacaccacc ttcaactcca gcagtgaagc tgagcagaag acacagcgct    780
tctacctatc ttgcctacag gtggagcgca ttgaggagct gggagcccag ccactgagag    840
acctcattga agaagattggt ggttggaaca ttacggggcc ctgggaccag acaactttta   900
tggaggtgtt gaaggcagta gcagggacct acagggccac ccattcttc accgtctaca    960 tcagtgccga ctctaagagt tccaacagca atgttatcca ggtggaccag tctgggctct    1020
ttctgccctc tcgggattac tacttaaaca gaactgccaa tgagaaagtg ctcactgcct    1080
atctggatta catggaggaa ctggggatgc tgctgggtgg gcggcccacc tccacgaggg    1140
agcagatgca gcaggtgctg gagttggaga tacagctggc caacatcaca gtgccccagg    1200
accagcggcg cgacgaggag aagatctacc acaagatgag catttcggag ctgcaggctc    1260
tggcgccctc catggactgg cttgagttcc tgtctttctt gctgtcacca ttggagttga    1320
gtgactctga gcctgtggtg gtgtatggga tggattattt gcagcaggtg tcagagctca    1380
tcaaccgcac ggaaccaagc atcctgaaca attacctgat ctggaacctg gtgcaaaaga    1440
caacctcaag cctggaccga cgctttgagt ctgcacaaga aagctgctg gagaccctct      1500 atggcactaa gaagtcctgt gtgccgaggt ggcagacctg catctccaac acggatgacg    1560
cccttggctt tgctttgggg tccctcttcg tgaaggccac gtttgaccgg caaagcaaag    1620
aaattgcaga ggggatgatc agcgaaatcc ggaccgcatt tgaggaggcc ctgggacagc    1680
tggtttggat ggatgagaag acccgccagg cagccaagga gaaagcagat gccatctatg    1740
atatgattgg tttcccagac tttatcctgg agcccaaaga gctggatgat gtttatgacg    1800
ggtacgaaat ttctgaagat tcttttcttcc aaaacatgtt gaatttgtac aacttctctg   1860
ccaaggttat ggctgaccag ctccgcaagc ctcccagccg agaccagtgg agcatgaccc    1920
cccagacagt gaatgcctac taccttccaa ctaagaatga gatcgtcttc cccgctggca    1980
tcctgcaggc cccctttctat gcccgcaacc accccaaggc cctgaacttc ggtggcatcg    2040
gtgtggtcat gggccatgag ttgacgcatg ccttttgatga ccaagggcgc gagtatgaca    2100
aagaagggaa cctgcggccc tggtggcaga atgagtccct gcagccttc cggaaccaca    2160 cggcctgcat ggaggaacag tacaatcaat accaggtcaa tggggagagg ctcaacggcc    2220
gccagacgct gggggagaac attgctgaca cgggggggct gaaggctgcc tacaatgctt    2280
acaaagcatg gctgagaaag catgggggagg agcagcaact gccagccgtg gggctcacca    2340
accaccagct cttcttcgtg ggatttgccc aggtgtggtg ctcggtccgc acaccagaga    2400
gctctcacga ggggctggtg accgaccccc acagccctgc cgcttccgc gtgctgggca    2460 ctctctccaa ctcccgtgac ttcctgcggc acttcggctg ccctgtcggc tccccatga    2520 acccagggca gctgtgtgag gtgtggtaga cctggatcag gggagaaatg cccagctgtc    2580
accagacctg ggcagctct cctgacaaag ctgtttgctc ttgggttggg aggaagcaaa     2640
tgcaagctgg gctgggtcta gtccctcccc cccacaggtg acatgagtac agaccctcct    2700
```

```
caatcaccac attgtgcctc tgctttgggg gtgcccctgc ctccagcaga gcccccacca   2760
ttcactgtga catctttccg tgtcaccctg cctggaagag gtctggtgg ggaggccagt    2820 tcccatagga aggagtctgc ctcttctgtc cccaggctca ctcagcctgg cggccatggg   2880
gcctgccgtg cctgccccac tgtgacccac aggcctgggt ggtgtacctc ctggacttct   2940
ccccaggctc actcagtgcg cacttagggg tggactcagc tctgtctggc tcaccctcac   3000
gggctacccc cacctcaccc tgtgctcctt gtgccactgc tcccagtgct gctgctgacc   3060
ttcactgaca gctcctagtg gaagcccaag ggcctctgaa agcctcctgc tgcccactgt   3120
ttccctgggc tgagagggga agtgcatatg tgtagcgggt actggttcct gtgtcttagg   3180
gcacaagcct tagcaaatga ttgattctcc ctggacaaag caggaaagca gatagagcag   3240
ggaaaaggaa gaacagagtt tattttaca gaaaagaggg tgggagggtg tggtcttggc    3300
ccttatagga ccctgtgcca ataaacagac atgcatccgt caaaaaaaaa aaaaaaaaaa   3360
aaaaaaaaaa aaaaaa                                                   3377
```

<210> SEQ ID NO 2
<211> LENGTH: 811
<212> TYPE: PRT
<213> ORGANISM: Human

<400> SEQUENCE: 2

```
Met Asn Val Ala Leu Gln Glu Leu Gly Ala Gly Ser Asn Met Val Glu
 1               5                  10                  15

Tyr Lys Arg Ala Thr Leu Arg Asp Glu Asp Ala Pro Glu Thr Pro Val
                20                  25                  30

Glu Gly Gly Ala Ser Pro Asp Ala Met Glu Val Gly Lys Gly Ala Ser
            35                  40                  45

Pro Phe Ser Pro Gly Pro Ser Pro Gly Met Thr Pro Gly Thr Pro Arg
        50                  55                  60

Ser Ser Gly Leu Phe Trp Arg Val Thr Cys Pro His Leu Arg Ser Ile
65                  70                  75                  80

Ser Gly Leu Cys Ser Arg Thr Met Val Gly Phe Gln Lys Gly Thr Arg
                85                  90                  95

Gln Leu Leu Gly Ser Arg Thr Gln Leu Glu Leu Val Leu Ala Gly Ala
            100                 105                 110

Ser Leu Leu Leu Ala Ala Leu Leu Gly Cys Leu Val Ala Leu Gly
        115                 120                 125

Val Gln Tyr His Arg Asp Pro Ser His Ser Thr Cys Leu Thr Glu Ala
    130                 135                 140

Cys Ile Arg Val Ala Gly Lys Ile Leu Glu Ser Leu Asp Arg Gly Val
145                 150                 155                 160

Ser Pro Cys Glu Asp Phe Tyr Gln Phe Ser Cys Gly Gly Trp Ile Arg
                165                 170                 175

Arg Asn Pro Leu Pro Asp Gly Arg Ser Arg Trp Asn Thr Phe Asn Ser
            180                 185                 190

Leu Trp Asp Gln Asn Gln Ala Ile Leu Lys His Leu Leu Glu Asn Thr
        195                 200                 205

Thr Phe Asn Ser Ser Ser Glu Ala Glu Gln Lys Thr Gln Arg Phe Tyr
    210                 215                 220

Leu Ser Cys Leu Gln Val Glu Arg Ile Glu Glu Leu Gly Ala Gln Pro
225                 230                 235                 240

Leu Arg Asp Leu Ile Glu Lys Ile Gly Gly Trp Asn Ile Thr Gly Pro
                245                 250                 255
```

-continued

```
Trp Asp Gln Asp Asn Phe Met Glu Val Leu Lys Ala Val Ala Gly Thr
            260                 265                 270
Tyr Arg Ala Thr Pro Phe Phe Thr Val Tyr Ile Ser Ala Asp Ser Lys
        275                 280                 285
Ser Ser Asn Ser Asn Val Ile Gln Val Asp Gln Ser Gly Leu Phe Leu
    290                 295                 300
Pro Ser Arg Asp Tyr Tyr Leu Asn Arg Thr Ala Asn Glu Lys Val Leu
305                 310                 315                 320
Thr Ala Tyr Leu Asp Tyr Met Glu Glu Leu Gly Met Leu Leu Gly Gly
                325                 330                 335
Arg Pro Thr Ser Thr Arg Glu Gln Met Gln Gln Val Leu Glu Leu Glu
            340                 345                 350
Ile Gln Leu Ala Asn Ile Thr Val Pro Gln Asp Gln Arg Arg Asp Glu
        355                 360                 365
Glu Lys Ile Tyr His Lys Met Ser Ile Ser Glu Leu Gln Ala Leu Ala
    370                 375                 380
Pro Ser Met Asp Trp Leu Glu Phe Leu Ser Phe Leu Ser Pro Leu
385                 390                 395                 400
Glu Leu Ser Asp Ser Glu Pro Val Val Tyr Gly Met Asp Tyr Leu
                405                 410                 415
Gln Gln Val Ser Glu Leu Ile Asn Arg Thr Glu Pro Ser Ile Leu Asn
            420                 425                 430
Asn Tyr Leu Ile Trp Asn Leu Val Gln Lys Thr Thr Ser Ser Leu Asp
        435                 440                 445
Arg Arg Phe Glu Ser Ala Gln Glu Lys Leu Leu Glu Thr Leu Tyr Gly
    450                 455                 460
Thr Lys Lys Ser Cys Val Pro Arg Trp Gln Thr Cys Ile Ser Asn Thr
465                 470                 475                 480
Asp Asp Ala Leu Gly Phe Ala Leu Gly Ser Leu Phe Val Lys Ala Thr
                485                 490                 495
Phe Asp Arg Gln Ser Lys Glu Ile Ala Glu Gly Met Ile Ser Glu Ile
            500                 505                 510
Arg Thr Ala Phe Glu Glu Ala Leu Gly Gln Leu Val Trp Met Asp Glu
        515                 520                 525
Lys Thr Arg Gln Ala Ala Lys Glu Lys Ala Asp Ala Ile Tyr Asp Met
    530                 535                 540
Ile Gly Phe Pro Asp Phe Ile Leu Glu Pro Lys Glu Leu Asp Asp Val
545                 550                 555                 560
Tyr Asp Gly Tyr Glu Ile Ser Glu Asp Ser Phe Phe Gln Asn Met Leu
                565                 570                 575
Asn Leu Tyr Asn Phe Ser Ala Lys Val Met Ala Asp Gln Leu Arg Lys
            580                 585                 590
Pro Pro Ser Arg Asp Gln Trp Ser Met Thr Pro Gln Thr Val Asn Ala
        595                 600                 605
Tyr Tyr Leu Pro Thr Lys Asn Glu Ile Val Phe Pro Ala Gly Ile Leu
    610                 615                 620
Gln Ala Pro Phe Tyr Ala Arg Asn His Pro Lys Ala Leu Asn Phe Gly
625                 630                 635                 640
Gly Ile Gly Val Val Met Gly His Glu Leu Thr His Ala Phe Asp Asp
                645                 650                 655
Gln Gly Arg Glu Tyr Asp Lys Gly Asn Leu Arg Pro Trp Trp Gln
            660                 665                 670
```

-continued

Asn Glu Ser Leu Ala Ala Phe Arg Asn His Thr Ala Cys Met Glu Glu
            675                 680                 685

Gln Tyr Asn Gln Tyr Gln Val Asn Gly Glu Arg Leu Asn Gly Arg Gln
        690                 695                 700

Thr Leu Gly Glu Asn Ile Ala Asp Asn Gly Gly Leu Lys Ala Ala Tyr
705                 710                 715                 720

Asn Ala Tyr Lys Ala Trp Leu Arg Lys His Gly Glu Glu Gln Gln Leu
                725                 730                 735

Pro Ala Val Gly Leu Thr Asn His Gln Leu Phe Phe Val Gly Phe Ala
            740                 745                 750

Gln Val Trp Cys Ser Val Arg Thr Pro Glu Ser Ser His Glu Gly Leu
            755                 760                 765

Val Thr Asp Pro His Ser Pro Ala Arg Phe Arg Val Leu Gly Thr Leu
            770                 775                 780

Ser Asn Ser Arg Asp Phe Leu Arg His Phe Gly Cys Pro Val Gly Ser
785                 790                 795                 800

Pro Met Asn Pro Gly Gln Leu Cys Glu Val Trp
                805                 810

<210> SEQ ID NO 3
<211> LENGTH: 19650
<212> TYPE: DNA
<213> ORGANISM: Human
<220> FEATURE:
<221> NAME/KEY: misc_feature
<222> LOCATION: (1)...(19650)
<223> OTHER INFORMATION: n = A,T,C or G

<400> SEQUENCE: 3
nnnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnnnnn nnnnnnnnnn nnnnnnnnnn     480
nnnnnnnnnn nnnnnnnnnn nnnnnnnnnn nnnnnnnnnn nnnnnnnnnn nnnnnnnnnn     540
nnnnnnnnnn nnnnnnnnnn nnnnnnnnnn nnnnnnnnnn nnnnnnnnnn nnnnnnnnnn     600
nnnnnnnnnn nnnnnnnnnn nnnnnnnnnn nnnnnnnnnn nnnnnnnnnn nnnnnnnnnn     660
nnnnnnnnnn nnnnnnnnnn nnnnnnnnnn nnnnnnnnnn nnnnnnnnnn nnnnnnnnnn     720
nnnnnnnnnn nnnnnnnnnn nnnnnnnnnn nnnnnnnnnn nnnnnnnnnn nnnnnnnnnn     780
nnnnnnnnnn nnnnnnnnnn nnnnnnnnnn nnnnnnnnnn nnnnnnnnnn nnnnnnnnnn     840
nnnnnnnnnn nnnnnnnnnn nnnnnnnnnn nnnnnnnnnn nnnnnnnnnn nnnnnnnnnn     900
nnnnnnnnnn nnnnnnnnnn nnnnnnnnnn nnnnnnnnnn nnnnnnnnnn nnnnnnnnnn     960
nnnnnnnnnn nnnnnnnnnn nnnnnnnnnn nnnnnnnnnn nnnnnnnnnn nnnnnnnnnn    1020
nnnnnncacc ttagacttga caggcctgct tagtcggact ctaaagcacc cctttgcttt    1080
tcgttaaata ttgcttggtg ttagtttttt ttctccttgt aaatctccca aataaaacgg    1140
tttgctttcc ccaagttaga agtgttagca cgtctttttct ttaaatatct gtgcatggct    1200

```
gttttttttcc ctgccaattt gtcaccatct gtaaccctcc ctttatgaga cgatctgatg    1260
acagcagtta tcttggagag tagaagtgtg gtcttgaagc gccatggaag agtagagtca    1320
gtgtatgctg tgtgtgtgtg gagtgtatgc tcccectgca cttggtgtgt gtacatacag    1380
aaacacagtg tgcgtgtgtg ttggctctgg gtgtgttgtg cgtgtgtaca ctgtgtgtga    1440
gtatgcagtg tgtgtacatt ctgtgggcat ctcgtgtgtg tgtggactgt gtgctgggcg    1500
tcgtgcctgc ccgtgtcctt ggcgccttgg cgtctatgcg ttctctgcac ataggtaggt    1560
accacgtgca caccctgaat gtgagtgaac tgcctgtgtg ctatgtattt gccggctgaa    1620 gagggggctgt gtggactact gggggaagac gttcctcang agggcataat ttctctaaag    1680
tgcttaaagg ggatggagag agcctgaaat ttggggggaag taggccaagg agtattatca    1740
acgtctgggc ctggttgaat tcattactt ttcctaggaa agtaaattat gggtggcttg    1800
aaggagggtg ctgctgagat gggggggcgga ccatgaagcg tggagggggtc tccggtgttg    1860 ctggagggca gctggagcct gcggagagcc tcggcgcgct cctccctctc ccccacccctc    1920 cccccacccc gggcgggggct ccgcgtgggg cggtggactc gggcgggggg ggggggcggcc    1980 gcggccgagc gggggtgctg cgcggcggcc gtgatggctg gtgacggcgg ggccgggcag    2040
gggaccgggg ccgcggcccg ggagcgggcc agctgccggg agccctgaat caccgcctgg    2100
cccgactcca ccatgaacgt cgcgctgcag gagctggag ctggcagcaa cgtgagtggg    2160
ggccccgggc tccacgggag gggactgggg ggaggggggac gaggcagagg ggtcggccgc    2220 ggagggggcag gcggtgcccg gctcgcggag gtaaggctgc ctcccgggcc tggtggaggg    2280
gtgatagaga gaccccgggc ccgagagcag ggcaggtggg aagggaaggg ccctcttagc    2340
agggcggagg ggtccgcgag gcaggagca ctggggcagg gtcgtgggca aatagccctc    2400
tctgcctgac ctcggttggc aaccccgact gtctggcaga tggtggagta caaacgggcc    2460
acgcttcgga tgaagacgc acccgagacc cccgtagagg gcggggcctc cccggacgcc    2520
atggaggtgg gcaagggggc ttccccttc tcaccaggcc ccagccctgg catgacgcct    2580
ggcacaccca ggagctctgg gctgttctgg agggtcatct gccccacct ccgctccatc    2640 tctggcctct gctctaggac tatggtgagg cgatgctaag ccgtgacgtt gcacaaaaca    2700
gactcaaggc tcaactcact ggctggcctc attgccccccg ggcccagagt taaccctgtg    2760
gctctgaaaa ctgcctgtgg cttcacccctc tggtaatctt ggatccctgc cctgcatctc    2820
agtcactctc tgtcccccctg tgttccccag gtgggattcc agaagggggac aagacagctg    2880 ttaggctcac gcacgcagct ggagctggtc ttagcaggtg cctctctact gctggctgca    2940
ctgcttctgg gctgccttgt ggccctaggg gtccagtacc acagaggtag gtgggcccac    3000
actcttcgtc agtattcata actaggggtt ctggaggcct aagggcctct aagattttca    3060
cttgtgggaa ccaagccttc cctgcagaaa agccccggc tttgctttct cttcccaacc    3120
ttcctgctgt catggcccctt gcagagtttg cctcttccag acagacagac tgacagtctc    3180
ctaccctccg gccatgttcc ctaccacaga cccatcccac agcacctgcc ttacagaggc    3240
ctgcattcga gtggctggaa aaatcctgga gtccctggac cgagggggtga gcccctgtga    3300 ggacttttac cagttctcct gtgnnnnnnn nnnnnnnnnn nnnnnnnnnn nnnnnnnnnn    3360
nnnnnnnnnn nnnnnnnnnn nnnnnnnnnn nnnnnnnnnn nnnnnnnnnn nnnnnnnnnn    3420
nnnnnnnnnn nnnnnnnnnn nnnnnnnnnn nnnnnnnnnc ttagcaaata ggcagtgtcc    3480
catgaatgag gaagtggatg gttctgtgaa cactcccaga gggtggggag gcagagagca    3540
ggggactatt gagaagtgca gatggttttg atgggggcag aactctgggt acaatggagg    3600
```

-continued

```
gccgcttctc tgcactctgt ttggagcact gtcgtggtgt ggtagacacc agggagcctg    3660
tactgcttag atatccttgg gtctccatgg acagggagag gaagccacgg cttgctgttt    3720
cagacactct tcctgggtct gcgttagcag gactgctcat tgacaaggca aggagagaaa    3780
ccgagcaagg gccagggact cccccctcagc agttaacgta attgccacct ggatcctgtg    3840
ttctgcccca cagaaaacac caccttcaac tccagcagta agctgagca gaagacacag    3900 cgcttctacc tatcttgcct acaggtggag cgcattgagg agctgggagc ccagccactg    3960
agagacctca ttgagaaggt agggccactg agccggttga gggcagggga gcaggagagg    4020
ccttgagaga ggagatggcc caggaacgct ttgggagctc ctgcactaat cattccactt    4080
atggtctcta catagattgg tggttggaac attacgggc cctgggacca ggacaacttt    4140
atggaggtgt tgaaggcagt agcagggacc tacagggcca ccccattctt caccgtctac    4200
atcagtgccg actctaagag ttccaacagc aatgttatcc aggtgatgag ctgggaaagg    4260
gtggggagag acttagggac actttgctga gcccagactt ccctctcctg tgacaggcag    4320
gctgggctga cccccccggcc ccaccccctac ccccgctcgg gaattcaggt tcccatggtg    4380
gggaaagcga ggggctcacc tcctttcctt gacattgcag gtggaccagt ctgggctctt    4440
tctgccctct cgggattact acttaaacag aactgccaat gagaaagtaa ggaacatctt    4500
ccgaaccccc atccctaccc ctggctgagc tgggctgatc cctgttgact tttccctttg    4560
ccaagggtca gagcagggaa ggtgagccta tcctgtcacc tagtgaacaa actgcccctc    4620
ctttctttct tctttcttc ctccctccct cccttttcttc ccctttttcct tccttccttc    4680 ctcttattct tctagtaggt ttcatagaca cctactgtgt gccaggtcca gtgggggaat    4740
tctgagatat aagtttnccg agcccattgc cagcaggaga ggggatcctt tagagtcgca    4800
caaacaggtc agtcaagtct aaagacnnnn nnnnnnnnnn nnnnnnnnnn nnnnnnnnnn    4860
nnnnnnnnnn nnnnnnnnnn nnnnnnnnnn nnnnnnnnnn nnnnnnnnnn nnnnnnnnnn    4920
nnnnnnnnnn nnnnnnnnnn nnnnnnnnnn nnnnnnnnnn nnnnnnnnnn nnnnnnnnnn    4980
nnnnnnnnnn nnnnnnnnnn nnnnnnnnnn nnnnnnnnnn nnnnnnnnnn nnnnnnnnnn    5040
nnnnnnnnnn nnnnnnnnnn nnnnnnnnnn nnnnnnnnnn nnnnnnnnnn nnnnnnnnnn    5100
nnnnnnnnnn nnnnnnnnnn gcctgnactt gcatgcaccg cggttcggct nctagnagna    5160 tcccccccact gcactccagc ctgggtgacg gagagagact ccgactcaaa aaaaaaaaa    5220 aaaaagaaag aaaaagaaag aaggaacagt ttaaacaaaa gtgttgatga ggctgagcac    5280
agtggctcac acctgtaatc cccgcacttt gggaggctga ggccggcgga tcacttgagg    5340
ttaggagttc aagaccaggc tggcctacaa ggtgaaaacc cgtctctact aaaaatacaa    5400
aaattagcca ggcatggtgg tgtgcacctg taatctcagc tacttgggag gctgaggcaa    5460
agagaatcgc ttgaatccag gaggcagagg ttgcagtgag ctgagatggc accactgcac    5520
tccagcctgg gcaacagaac aagacttcat ctcaaaaaaa aaaaaaaaag tgttgacgag    5580
ggaaaggcta ggtgtgtctg gaccatggca agggtccac tgtggtaaaa tatagaactc    5640
aaggcagatg agaggctgga gaggtgggca ggaatgggtt atggagggga ccttgaatag    5700
cacactacgg agtttattct gtagctcccg gagagccatt gcatgctcca agtagggag    5760 ggagcgcant gctttgggaa gtcagtttgt ttggggtgtg aagagtanat gtgagaacnn    5820
nnnnnnnnnn nnnnnnnnnn nnnnnnnnnn nnnnnnnnnn nnnnnnnnnn nnnnnnnnnn    5880
nnnnnnnnnn nnnnnnnnnn nnnnnnnnnn nnnnnnnnnn nnnnnnnnnn nnnnnnnnnn    5940
```

-continued

| | |
|---|---|
| nnnnnnnnnn nnnnnnnnnn nnnnnnnnnn nnnnnnnnnn nnnnnnnnnn nnnnnnnnnn | 6000 |
| nnnnnnnnnn nnnnnnnnnn nnnnnnnnnn nnnnnnnnnn nnnnnnnnnn nnnnnnnnnn | 6060 |
| nnnnnnnnnn nnnnnnnnnn nnnnnnnnnn nnnnnnnnnn nnnnnnnnnn nnnnnnnnnn | 6120 |
| nnnnnnnnnn nnnnnnnnnn nnnnnnnnnn nnnnnnnnnn nnnnnnnnnn nnnnnnnnnn | 6180 |
| nnnnnnnnnn nnnnnnnnnn nnnnnnnnnn nnnnnnnnnn nnnnnnnnnn nnnnnnnnnn | 6240 |
| nnnnnnnnnn nnnnnnnnnn nnnnnnnnnn nnnnnnnnnn nnnnnnnnnn nnnnnnnnnn | 6300 |
| nnnnnnnnnn nnnnnnnnnn nnnnnnnnnn nnnnnnnnnn nnnnnnnnnn nnnnnnnnnn | 6360 |
| nnnnnnnnnn nnnnnnnnnn nnnnnnnnnn nnnnnnnnnn nnnnnnnnnn nnnnnnnnnn | 6420 |
| nnnnnnnnnn nnnnnnnnnn nnnnnnnnnn nnnnnnnnnn nnnnnnnnnn nnnnnnnnnn | 6480 |
| nnnnnnnnnn nnnnnnnnnn nnnnnnnnnn nnnnnnnnnn nnnnnnnnnn nnnnnnnnnn | 6540 |
| nnnnnnnnnn nnnnnnnnnn nnnnnnnnnn nnnnnnnnnn nnnnnnnnnn nnnnnnnnnn | 6600 |
| nnnnnnnnnn nnnnnnnnnn nnnnnnnnnn nnnnnnnnnn nnnnnnnnnn nnnnnnnnnn | 6660 |
| nnnnnnnnnn nnnnnnnnnn nnnnnnnnnn nnnnnnnnnn nnnnnnnnnn nnnnnnnnnn | 6720 |
| nnnnnnnnnn nnnnnnnnnn nnnnnnnnnn nnnnnnnnnn nnnnnnnnnn nnnnnnnnnn | 6780 |
| nnnnnnnnnn nnnnnnnnnn nnnnnnnnnn nnnnnnnnnn nnnnnnnnnn nnnnnnnnnn | 6840 |
| nnnnnnnnnn nnnnnnnnnn nnnnnnnnnn nnnnnnnnnn nnnnnnnnnn nnnnnnnnnn | 6900 |
| nnnnnnnnnn nnnnnnnnnn nnnnnnnnnn nnnnnnnnnn nnnnnnnnnn nnnnnnnnnn | 6960 |
| nnnnnnnnnn nnnnnnnnnn nnnnnnnnnn nnnnnnnnnn nnnnnnnnnn nnnnnnnnnn | 7020 |
| nnnnnnnnnn nnnnnnnnnn nnnnnnnnnn nnnnnnnnnn nnnnnnnnnn nnnnnnnnnn | 7080 |
| nnnnnnnnnn nnnnnnnnnn nnnnnnnnnn nnnnnnnnnn nnnnnnnnnn nnnnnnnnnn | 7140 |
| nnnnnnnnnn nnnnnnnnnn nnnnnnnnnn nnnnnnnnnn nnnnnnnnnn nnnnnnnnnn | 7200 |
| nnnnnnnnnn nnnnnnnnnn nnnnnnnnnn nnnnnnnnnn nnnnnnnnnn nnnnnnnnnn | 7260 |
| nnnnnnnnnn nnnnnnnnnn nnnnnnnnnn nnnnnnnnnn nnnnnnnnnn nnnnnnnnnn | 7320 |
| nnnnnnnnnn nnnnnnnnnn nnnnnnnnnn nnnnnnnnnn nnnnnnnnnn nnnnnnnnnn | 7380 |
| nnnnnnnnnn nnnnnnnnnn nnnnnnnnnn nnnnnnnnnn nnnnnnnnnn nnnnnnnnnn | 7440 |
| nnnnnnnnnn nnnnnnnnnn nnnnnnnnnn nnnnnnnnnn nnnnnnnnnn nnnnnnnnnn | 7500 |
| nnnnnnnnnn nnnnnnnnnn nnnnnnnnnn nnnnnnnnnn nnnnnnnnnn nnnnnnnnnn | 7560 |
| nnnnnnnnnn nnnnnnnnnn nnnnnnnnnn nnnnnnnnnn nnnnnnnnnn nnnnnnnnnn | 7620 |
| nnnnnnnnnn nnnnnnnnnn nnnnnnnnnn nnnnnnnnnn nnnnnnnnnn nnnnnnnnnn | 7680 |
| nnnnnnnnnn nnnnnnnnnn nnnnnnnnnn nnnnnnnnnn nnnnnnnnnn nnnnnnnnnn | 7740 |
| nnnnnnnnnn nnnnnnnnnn nnnnnnnnnn nnnnnnnnnn nnnnnnnnnn nnnnnnnnnn | 7800 |
| nnnnnnnnnn nnnnnnnnnn nnnnnnnnnn nnnnnnnnnn nnnnnnnnnn nnnnnnnnnn | 7860 |
| nnnnnnnnnn nnnnnnnnnn nnnnnnnnnn nnnnnnnnnn nnnnnnnnnn nnnnnnnnnn | 7920 |
| nnnnnnnnnn nnnnnnnnnn nnnnnnnnnn nnnnnnnnnn nnnnnnnnnn nnnnnnnnnn | 7980 |
| nnnnnnnnnn nnnnnnnnnn nnnnnnnnnn nnnnnnnnnn nnnnnnnnnn nnnnnnnnnn | 8040 |
| nnnnnnnnnn nnnnnnnnnn nnnnnnnnnn nnnnnnnnnn nnnnnnnnnn nnnnnnnnnn | 8100 |
| nnnnnnnnnn nnnnnnnnnn nnnnnnnnnn nnnnnnnnnn nnnnnnnnnn nnnnnnnnnn | 8160 |
| nnnnnnnnnn nnnnnnnnnn nnnnnnnnnn nnnnnnnnnn nnnnnnnnnn nnnnnnnnnn | 8220 |
| nnnnnnnnnn nnnnnnnnnn nnnnnnnnnn nnnnnnnnnn nnnnnnnnnn nnnnnnnnnn | 8280 |
| nnnnnnnnnn nnnnnnnnnn nnnnnnnnnn nnnnnnnnnn nnnnnnnnnn nnnnnnnnnn | 8340 |

```
nnnnnnnnnn nnnnnnnnnn nnnnnnnnnn nnnnnnnnnn nnnnnnnnnn nnnnnnnnnn      8400
nnnnnnnnnn nnnnnnnnnn nnnnnnnnnn nnnnnnnnnn nnnnnnnnnn nnnnnnnnnn      8460
nnnnnnnnnn nnnnnnnnnn nnnnnnnnnn nnnnnnnnnn nnnnnnnnnn nnnnnnnnnn      8520
nnnnnnnnnn nnnnnnnnnn nnnnnnnnnn nnnnnnnnnn nnnnnnnnnn nnnnnnnnnn      8580
nnnnnnnnnn nnnnnnnnnn nnnnnnnnnn nnnnnnnnnn nnnnnnnnnn nnnnnnnnnn      8640
nnnnnnnnnn nnnnnnnnnn nnnnnnnnnn nnnnnnnnnn nnnnnnnnnn nnnnnnnnnn      8700
nnnnnnnnnn nnnnnnnnnn nnnnnnnnnn nnnnnnnnnn nnnnnnnnnn nnnnnnnnnn      8760
nnnnnnnnnn nnnnnnnnnn nnnnnnnnnn nnnnnnnnnn nnnnnnnnnn nnnnnnnnnn      8820
nnnnnnnnnn nnnnnnnnnn nnnnnnnnnn nnnnnnnnnn nnnnnnnnnn nnnnnnnnnn      8880
nnnnnnnnnn nnnnnnnnnn nnnnnnnnnn nnnnnnnnnn nnnnnnnnnn nnnnnnnnnn      8940
nnnnnnnnnn nnnnnnnnnn nnnnnnnnnn nnnnnnnnnn nnnnnnnnnn nnnnnnnnnn      9000
nnnnnnnnnn nnnnnnnnnn nnnnnnnnnn nnnnnnnnnn nnnnnnnnnn nnnnnnnnnn      9060
nnnnnnnnnn nnnnnnnnnn nnnnnnnnnn nnnnnnnnnn nnnnnnnnnn nnnnnnnnnn      9120
nnnnnnnnnn nnnnnnnnnn nnnnnnnnnn nnnnnnnnnn nnnnnnnnnn nnnnnnnnnn      9180
nnnnnnnnnn nnnnnnnnnn nnnnnnnnnn nnnnnnnnnn nnnnnnnnnn nnnnnnnnnn      9240
nnnnnnnnnn nnnnnnnnnn nnnnnnnnnn nnnnnnnnnn nnnnnnnnnn nnnnnnnnnn      9300
nnnnnnnnnn nnnnnnnnnn nnnnnnnnnn nnnnnnnnnn nnnnnnnnnn nnnnnnnnnn      9360
nnnnnnnnnn nnnnnnnnnn nnnnnnnnnn nnnnnnnnnn nnnnnnnnnn nnnnnnnnnn      9420
nnnnnnnnnn nnnnnnnnnn nnnnnnnnnn nnnnnnnnnn nnnnnnnnnn nnnnnnnnnn      9480
nnnnnnnnnn nnnnnnnnnn nnnnnnnnnn nnnnnnnnnn nnnnnnnnnn nnnnnnnnnn      9540
nnnnnnnnnn nnnnnnnnnn nnnnnnnnnn nnnnnnnnnn nnnnnnnnnn nnnnnnnnnn      9600
nnnnnnnnnn nnnnnnnnnn nnnnnnnnnn nnnnnnnnnn nnnnnnnnnn nnnnnnnnnn      9660
nnnnnnnnnn nnnnnnnnnn nnnnnnnnnn nnnnnnnnnn nnnnnnnnnn nnnnnnnnnn      9720
nnnnnnnnnn nnnnnnnnnn nnnnnnnnnn nnnnnnnnnn nnnnnnnnnn nnnnnnnnnn      9780
nnnnnnnnnn nnnnnnnnnn nnnnnnnnnn nnnnnnnnnn nnnnnnnnnn nnnnnnnnnn      9840
nnnnnnnnnn nnnnnnnnnn nnnnnnnnnn nnnnnnnnnn nnnnnnnnnn nnnnnnnnnn      9900
nnnnnnnnnn nnnnnnnnnn nnnnnnnnnn nnnnnnnnnn nnnnnnnnnn nnnnnnnnnn      9960
nnnnnnnnnn nnnnnnnnnn nnnnnnnnnn nnnnnnnnnn nnnnnnnnnn nnnnnnnnnn     10020
nnnnnnnnnn nnnnnnnnnn nnnnnnnnnn nnnnnnnnnn nnnnnnnnnn nnnnnnnnnn     10080
nnnnnnnnnn nnnnnnnnnn nnnnnnnnnn nnnnnnnnnn nnnnnnnnnn nnnnnnnnnn     10140
nnnnnnnnnn nnnnnnnnnn nnnnnnnnnn nnnnnnnnnn nnnnnnnnnn nnnnnnnnnn     10200
nnnnnnnnnn nnnnnnnnnn nnnnnnnnnn nnnnnnnnnn nnnnnnnnnn nnnnnnnnnn     10260
nnnnnnnnnn nnnnnnnnnn nnnnnnnnnn nnnnnnnnnn nnnnnnnnnn nnnnnnnnnn     10320
nnnnnnnnnn nnnnnnnnnn nnnnnnnnnn nnnnnnnnnn nnnnnnnnnn nnnnnnnnnn     10380
nnnnnnnnnn nnnnnnnnnn nnnnnnnnnn nnnnnnnnnn nnnnnnnnnn nnnnnnnnnn     10440
nnnnnnnnnn nnnnnnnnnn nnnnnnnnnn nnnnnnnnnn nnnnnnnnnn nnnnnnnnnn     10500
nnnnnnnnnn nnnnnnnnnn nnnnnnnnnn nnnnnnnnnn nnnnnnnnnn nnnnnnnnnn     10560
nnnnnnnnnn nnnnnnnnnn nnnnnnnnnn nnnnnnnnnn nnnnnnnnnn nnnnnnnnnn     10620
nnnnnnnnnn nnnnnnnnnn nnnnnnnnnn nnnnnnnnnn nnnnnnnnnn nnnnnnnnnn     10680
```

-continued

| | | | | | | |
|---|---|---|---|---|---|---|
| nnnnnnnnnn | nnnnnnnnnn | nnnnnnnnnn | nnnnnnnnnn | nnnnnnnnnn | nnnnnnnnnn | 10740 |
| nnnnnnnnnn | nnnnnnnnnn | nnnnnnnnnn | nnnnnnnnnn | nnnnnnnnnn | nnnnnnnnnn | 10800 |
| nnnnnnnnnn | nnnnnnnnnn | nnnnnnnnnn | nnnnnnnnnn | nnnnnnnnnn | nnnnnnnnnn | 10860 |
| nnnnnnnnnn | nnnnnnnnnn | nnnnnnnnnn | nnnnnnnnnn | nnnnnnnnnn | nnnnnnnnnn | 10920 |
| nnnnnnnnnn | nnnnnnnnnn | nnnnnnnnnn | nnnnnnnnnn | nnnnnnnnnn | nnnnnnnnnn | 10980 |
| nnnnnnnnnn | nnnnnnnnnn | nnnnnnnnnn | nnnnnnnnnn | nnnnnnnnnn | nnnnnnnnnn | 11040 |
| nnnnnnnnnn | nnnnnnnnnn | nnnnnnnnnn | nnnnnnnnnn | nnnnnnnnnn | nnnnnnnnnn | 11100 |
| nnnnnnnnnn | nnnnnnnnnn | nnnnnnnnnn | nnnnnnnnnn | nnnnnnnnnn | nnnnnnnnnn | 11160 |
| nnnnnnnnnn | nnnnnnnnnn | nnnnnnnnnn | nnnnnnnnnn | nnnnnnnnnn | nnnnnnnnnn | 11220 |
| nnnnnnnnnn | nnnnnnnnnn | nnnnnnnnnn | nnnnnnnnnn | nnnnnnnnnn | nnnnnnnnnn | 11280 |
| nnnnnnnnnn | nnnnnnnnnn | nnnnnnnnnn | nnnnnnnnnn | nnnnnnnnnn | nnnnnnnnnn | 11340 |
| nnnnnnnnnn | nnnnnnnnnn | nnnnnnnnnn | nnnnnnnnnn | nnnnnnnnnn | nnnnnnnnnn | 11400 |
| nnnnnnnnnn | nnnnnnnnnn | nnnnnnnnnn | nnnnnnnnag | ttccaggccc | acccttgggc | 11460 |
| caaacatgtt | gaagaccgcc | atgctgtagc | tagaacttac | aaaagatgta | agcctgggca | 11520 |
| taggtggccg | ggtgccgttg | tggtcgccac | gctatcttgg | ggagggatta | agggcaagga | 11580 |
| aaattcacct | tgaggcccaa | ggaaggcaca | agggttatca | cgtgaagccg | aggatcacca | 11640 |
| tcaccatgca | ctaacacgcc | ttgggcaagc | acgaagcgag | gagttgccat | ctcaaaacaa | 11700 |
| aaacgaaaaa | caaacaaaca | aatgctaat | caactgtcat | tggtaaggct | tctggtcaac | 11760 |
| agtatgctgt | caatagttaa | gttttggggc | tgggcgcagt | ggctcacgcc | tgtaatccca | 11820 |
| gcactttggg | aggccaaagc | gggtagatca | cctgaggtca | ggagtcgaga | ctagcctggc | 11880 |
| caacatggcg | aaacccagtc | tctactaaaa | atataaaaat | tagccaggcg | tggtggtggg | 11940 |
| cacttgtaat | cccagctact | caggaagctg | aggcagaact | gcttgaactg | ggaagtggag | 12000 |
| gttgcagtga | gccgagatcg | tgccattgca | ttccagcctg | ggcgacaaga | gcaaaactcc | 12060 |
| atctcaaaaa | aaaaaaaaaa | aaaaaagtt | gttttggggg | agtcaaaaat | gaggccaggc | 12120 |
| gcagtggctc | atgcctgtaa | tcacagcact | ttgggaggcc | gaggcgggtg | gatcacctga | 12180 |
| ggtcaggagt | tcgtgaccag | cttggccaac | ctggtgaaac | cccgtctcta | ctaaaaatac | 12240 |
| aaaaattagc | cgggcatggt | ggcgggcgcc | cgtaatctca | gctacttggg | cggctgaggc | 12300 |
| aggagaattg | cttcaacccg | ggaggcagag | gttgcaatga | gctgagatcg | cgccactgca | 12360 |
| ctccagcctt | ggcgacagag | ggagactcca | tgtcaaatta | aaaaaaagac | cccaggattt | 12420 |
| tggactgtgc | agggtcggt | gccccaaacc | cccacgttgt | tcaaggtcaa | ctgtacactg | 12480 |
| tcatagtcgg | gaaaacttca | tcactgcagc | tgctcctgtt | tcttgaaacc | tgaagcggga | 12540 |
| aactggatcc | tgggacacta | ctgccccta | tcgcctgttg | gtcttcaaag | aaataatccc | 12600 |
| ttcaattttg | caaggcctgt | ggtgtcattc | ccttttaaca | gataaggaaa | ccgaggccag | 12660 |
| gacgtggtgg | aaaataatca | aggtcacaca | tctatgtgca | aaagtggagt | aacaacccag | 12720 |
| gctcctcatt | cccaggtcag | tccagtgacc | tcaattgaca | tgaaatgtgt | gaggtccttc | 12780 |
| tgtggccctg | tggcagggcc | tgaagaggac | agcgtatgta | aatcaagtct | tgtgccttca | 12840 |
| tgagtgaggc | agagtagaaa | ataacagtaa | ttcactagga | ccgaatctgc | attgtaaaca | 12900 |
| gagaggaaag | ggctagtatt | tggcagaagg | atgtcaagga | acattttaga | gataagaggt | 12960 |
| gacatttggg | ttctgaggga | tgagtaggag | tgtgccaggg | tgcaaaggat | gaaaagacag | 13020 |
| ctctagcagc | tggtaagggc | taaggggcat | ggagaaacag | caagactttg | gggaactggt | 13080 |

```
agaattctaa ttctggaaaa tttgaacaag gtaatttttt gtgtgtggtt aaggtattac    13140
atacatacag taaaataaaa tgcaatagtt gctgggtgtg gaggctcacg cctgttaatc    13200
ccagtacttt ggaaggcaga ggcgggtgga tcatctgaag gtcaggagtt cgagaccagc    13260
ctgaccaaca tggtgaaaac ccgtctctac taaaaataca aaattaccct gggtgtggtg    13320
gcaggcgccc gtaatcccag ctacttggga ggctaaggga aagaatagc ttgaaacccg    13380 gaggtggagg ttgcagtgag ctgagattgc actattgcgc tccagcctgg gtgacaagag    13440
tgaaaagctg tctcaaaata aaataaaaat gtaatagtct aattgatttt tttaaaaaat    13500
gtagacatcc acgtatctac cacctaggta aagatactag agattccagc aacctgggag    13560
gatccctcgt gcccctttca ggtctatatg agcctccacc gttccccagt ccctggaag    13620 gagaggggt gggagaggca acatgaaacc taaaaaccag tgggcttcgc gcctgtaatc    13680
ccagctattg ggttggctga ggcaggagga tcacttgccc aggagttgga ggctgcagtg    13740
agctatgatc gcgccaccgc actccagcct gggcgacaga tcaagacccc atctctaagc    13800
aaacaaacaa ataaacaccc ctcaaaaccc atggcttcag gcctggcgcg gtagcttact    13860
tctgtaatct cagcactttg ggaggccgag gagggcggat cacttgaggt caggagttcc    13920
agaccagact ggccaacatg gcgaaacccc gtctctacta aaaataaaa aaaaaaaaa    13980 attggccggg cgcggtggct cacacctgta attaccagca gnnnnnnnnn nnnnnnnnnn    14040
nnnnnnnnnn nnnnnnnnnn nnnnnnnnnn nttttaaaga atgtagacat ccacgtatct    14100
accacctagg tagagatact agagattcca gcaacctggg aggatccctc gtgcgccttt    14160
caggtctata tgagcctcca ccgttcccca gtcccctgga aggagagggg gtgggagagg    14220
caacatgaaa cctaaaaacc agtgggcttc gcgcctgtaa tcccagctat gggttggct    14280 gaggcaggag gatcacttgc ccaggagttg gaggctgcag tgagctatga tcgcgccacc    14340
gcactccagc ctgggcgaca gatcaagacc ccatctctaa gcaaacaaac aaataaacac    14400
ccctcaaaac ccatggcttc aggcctggcg cggtagctta cttctgtaat ctcagcactt    14460
tgggaggtca aggtgggcgg atcacttgaa gtaaggagtt caagtaccat cctggctaac    14520
acggtgaaac cccgtctcta ctgaaaagac aaaaaattta gccgggcgtg gtggcgggcg    14580
cctttagtct cagctactcg ggaggctgag gcaggagaat ggcgtgaacc cgggaggtgg    14640
agcttgcagt gagctgagat cgcaccactg cactccagtc tgggtgacag agtgagactc    14700
catctcaaaa aaaaaaaaa agaagtcaaa gtagtagaaa ctgctgatag actgaatgtg    14760
gggggttagg gagatggagg aagctgagtg actcccaggt ttcttgcatg ggggactgac    14820
tggatataaa attagttgtg ggccgggcac ggtggctcat gcctttaatc ccagcacttt    14880
gggaggccaa gcgggcaga tcacttgagc tcaggagttc aagaccagcc tgggaaacat    14940
ggtgagaccc cttctgtaag ggnnnnnnnn nnnnnnnnnn nnnnnnnnnn nnnnnnnnnn    15000
nnnnnnnnnn nnntgacctt tttttggctc tgntcggtca ctagcangca agttattggg    15060
agtctacaag attctttcac actatgccct caaaattgac tgttcatgta tgtgcagaca    15120
tatagaaaaa caacgggagc caggcgcggt ggctcacgcc ggtaatccca gcactttggg    15180
aggccaaggc gggtgaatca tgggtcagg agttcgagac cagcctggcc aacatggtga    15240 aaccctggtct ctactaaaaa tacaaaaaat tagccgggcg tggtggcggg tgtctgtaat    15300
cccagctact tgggaggctg aggcaggaga atcacttgaa cccaggaggc ggaggttgca    15360
gtgagccgag atcgcgccag tgcactccag cctgggcgac agagcaaaac tctgtctcaa    15420
```

-continued

```
aaaaaaaaaa aaaaaaaaga aaagaaaaga aaaacaactg gatgtaaatt gatgaacaaa    15480
tgaagtagtg ctgctttggg cagtgggatt ataagagtcc tttaaagttg tctatgtgtt    15540
tatgtttaac tatataacta gaagaaatat ttatttatta ggatatgata atggatgtgc    15600
ttaaagtatt acctgtaagg atgtttatgg tttttatggc aatgttgttt ataatagcag    15660
aaaatgagaa caggttaaat gtccaactat agggtaaagg aaaaataaat tgtggttagg    15720
atgggttgtg aggatcctta aatggctgat atatctttca gcaaaaaaag taggttacaa    15780
aaaatatata ccctatacaa cataattcca tattttatat gcatatcagg ggagggaaaa    15840
actctagaag tgggtaatca aaatgttaaa agaacttatc tatgaatgag tgctttataa    15900
ctggtctgtt cttcaattct caattttcca aattttctgt gaatgtcctc ttttcataat    15960
cagataaaaa tcattgcact aggctgggcg tggtggttca cgcttgtaat cccagcactt    16020
tgggaggctg aggcgggtgg atcacgtggt caggagttca agaccaacct ggccaagatg    16080
gtgaaacccc agctctacta aaaatacaaa aattacccgg gcatgatggc gggagcctgt    16140
aatcctagct acttgggagg ctgaggcagg agaatcgctt gaactcggga ggcggaggtt    16200
gcagtgagcc gagattgcgc cactgcactc catcctaggt aacacagcca gactctgtct    16260
caaaaaaaaa aaaaaatcat tgcactatat taaattataa ataatttga tgaacttatt    16320
gtcaattaaa atgtgtactt aattaagaaa aaagccagcc acaatcccag tacctttaca    16380
aatggtgttt ccttctcatc gtctccaggt gctcagccgt atttctttag tctagacgtt    16440
cccatttccc ctggtggac agggatgggg caccaagggt ggatgggtgg ggcagggatg    16500
cattcagtgc aggggaaggc tgactttacc tcctccctcc caggcagagg ggatgatcag    16560
cgaaatccgg accgcatttg aggaggccct gggacagctg gtttggatgg atgagaagac    16620
ccgccaggca gccaaggaga aagtgagcgg tggctagggt tggggcgcca tcttgaggtg    16680
gggttcaagg atacagtttt gctaggaacc tggggaagga aacaaaccct taacctggtc    16740
tcttcaggca gatgccatct atgatatgat tggtttccca gactttatcc tggagcccaa    16800
agagctggat gatgtttatg acgggtgag tacctacgct catcagtact gaacttcagc    16860
cctgtagagg gcactgttcc ctgggcttag aaattggggc tcaagcactg ggaaagaggt    16920
gcttgtcggt tcttttaga ggcagatgga ggtaaccagc attgttaaaa tgttggctct    16980
gtgacaggct gcaggccaaa cagcagtgaa atatagtgct aacgagccaa gatttggagt    17040
caagcctaat caaattctgt ttctacctct aactttgtaa ccttaacaaa atctctctag    17100
gccttggttt cattttctgt aaaatggggg tcctactagt gccttcctca tagggttgtt    17160
gtgagataaa tgaatacagt atgtaaaaaa acagcaccca taacataaat ggcctttaaa    17220
tattgccaat tatggtttac tagatatttt acagttgagg aaactgaggt ttggagagat    17280
actaatgagt agccaaactg gcgctattat cttctccaat ggattctctt gctctctgtc    17340
tacttcccaa cttaccacag aacaaannnn nnnnnnnnnn nnnnnnnnnn nnnnnnnnnn    17400
nnnnnnnnnn nnnnnnnnnn nnnnnnnnnn nnnnnnnnnn nnnnnnnnnn nnnnnnnnnn    17460
nnnnnnnnnn nnnnnnnnnn nnnnnnnnnn nnnnnnnnnn nnnnnnnnnn nnnnnnnnnn    17520
nnnnnnnnnn nnnnnnnnnn nnnnnnnnnn nnnnnnnnnn nnnnnnnnnn nnnnnnnnnn    17580
nnnnnnnnnn nnnnnnnnnn nnnnnnnnnn nnnnnnnnnn nnnnnnnnnn nnnnnnnnnn    17640
nnnnnnnnnn nnnnnnnnnn nnnnnnnnnn nnnnnnnnnn nnnnnnnnnn nnnnnnnnnn    17700
nnnnnnnnnn nnnnnnnnnn nnnnnnnnnn nnnnnnnnnn nnnnnnnnnn nnnnnnnnnn    17760
nnnnnnnnnn nnnnnnnnnn nnnnnnnnnn nnnnnnnnnn nnnnnnnnnn nnnnnnnnnn    17820
```

-continued

```
nnnnnnnnnn nnnnnnnnnn nnnnnnnnnn nnnnnnnnnn nnnnnnnnnn nnnnnnnnnn    17880
nnnnnnnnnn nnnnnnnnnn nnnnnnnnnn nnnnnnnnnn nnnnnnnnnn nnnnnnnnnn    17940
nnnnnnnnnn nnnnnnnnnn nnnnnnnnnn nnnnnnnnnn nnnnnnnnnn nnnnnnnnnn    18000
nnnnnnnnnn nnnnnnnnnn nnnnnnnnnn nnnnnnnnnn nnnnnnnnnn nnnnnnnnnn    18060
nnnnnnnnnn nnnnnnnnnn nnnnnnnnnn nnnnnnnnnn nnnnnnnnnn nnnnnnnnnn    18120
nnnnnnnnnn nnnnnnnnnn nnnnnnnnnn nnnnnnnnnn nnnnnnnnnn nnnnnnnnnn    18180
nnnnnnnnnn nnnnnnnnnn nnnnnnnnnn nnnnnnnnnn nnnnnnnnnn nnnnnnnnnn    18240
nnnnnnnnnn nnnnnnnnnn nnnnnnnnnn nnnnnnnnnn nnnnnnnnnn nnnnnnnnnn    18300
nnnnnnnnnn nnnnnnnnnn nnnnnnnnnn nnnnnnnnnn nnnnnnnnnn nnnnnnnnnn    18360
nnnnnnnnnn nnnnnnnnnn nnnnnnnnnn nnnnnnnnnn nnnnnnnnnn nnnnnnnnnn    18420
nnnnnnnnnn nnnnnnnnnn nnnnnnnnnn nnnnnnnnnn nnnnnnnnnn nnnnnnnnnn    18480
nnnnnnnnnn nnnnnnnnnn nnnnnnnnnn nnnnnnnnnn nnnnnnnnnn nnnnnnnnnn    18540
nnnnnnnnnn nnnnnnnnnn nnnnnnnnnn nnnnnnnnnn nnnnnnnnnn nnnnnnnnnn    18600
nnnnnnnnnn nnnnnnnnnn nnnnnnnnnn nnnnnnnnnn nnnnnnnnnn nnnnnnnnnn    18660
nnnnnnnnnn nnnnnnnnnn nnnnnnnnnn nnnnnnnnnn nnnnnnnnnn nnnnnnnnnn    18720
nnnnnnnnnn nnnnnnnnnn nnnnnnnnnn nnnnnnnnnn nnnnnnnnnn nnnnnnnnnn    18780
nnnnnnnnnn nnnnnnnnnn nnnnnnnnnn nnnnnnnnnn nnnnnagaat caccaacagc    18840
attggatgaa aataaagaag aacaagaggt tcgtttgaga ggaagccggg aaaattctct    18900
cgataaagaa atgcaagtgc gcgcgcggcg caaccactac aatagtgtgt cgtccacccc    18960
agagagtgaa ggggccccc cccgcccaa aggaaagggg tagtgtccac gccgctccac    19020
aaagagagag aaggaaagaa gtagttttcc ccccccggg gagaaacctt ggatggggct    19080
canccccccc tcttttttt tcccgcgaaa acccccccca aaagttttt tttaaaaaac    19140 aaaaagggg ggtttggttt tttgggcccc gtggcccctt tggtttaaat tgggagaaag    19200
agggcttaaa ggggggattc aagaaaaaac cccccccaa ttgccccaaa ttgtaatttc    19260
ctaaccccaa aagggggcccc taaaatttcc ggggaaaccc gtgtgggcaa tgcccccatta   19320 gtttacccaa tgcctttatt gacaaaggta gggcccatg gagtcgtccc ctctagccta    19380
gaattcccag tggctcctgc aagggccttg ggacattgat gtagcccaa gggccctgaa    19440 gtctgtggac cagggctggt ggggcactgc tgccccaag agacgagctc tggttttggt    19500
ggggtgcaaa ggtgagttct cctcagggcg cgagtatgac aaagaaggga actgcggccc    19560
tggtggcaga atgagtccct ggcagccttc cggaaccaca cggcctgcat ggaggaacag    19620
tacaatcaat accaggtcaa tggggagagg                                     19650
```

```
<210> SEQ ID NO 4
<211> LENGTH: 765
<212> TYPE: PRT
<213> ORGANISM: Human

<400> SEQUENCE: 4

Met Asn Val Ala Leu Gln Glu Leu Gly Ala Gly Ser Asn Met Val Glu
 1               5                  10                  15

Tyr Lys Arg Ala Thr Leu Arg Asp Glu Asp Ala Pro Glu Thr Pro Val
                20                  25                  30

Glu Gly Gly Ala Ser Pro Asp Ala Met Glu Val Gly Phe Gln Lys Gly
            35                  40                  45
```

-continued

```
Thr Arg Gln Leu Leu Gly Ser Arg Thr Gln Leu Glu Leu Val Leu Ala
    50                  55                  60
Gly Ala Ser Leu Leu Ala Ala Leu Leu Gly Cys Leu Val Ala
 65                  70                  75                  80
Leu Gly Val Gln Tyr His Arg Asp Pro Ser His Ser Thr Cys Leu Thr
                     85                  90                  95
Glu Ala Cys Ile Arg Val Ala Gly Lys Ile Leu Glu Ser Leu Asp Arg
                100                 105                 110
Gly Val Ser Pro Cys Glu Asp Phe Tyr Gln Phe Ser Cys Gly Gly Trp
            115                 120                 125
Ile Arg Arg Asn Pro Leu Pro Asp Gly Arg Ser Arg Trp Asn Thr Phe
        130                 135                 140
Asn Ser Leu Trp Asp Gln Asn Gln Ala Ile Leu Lys His Leu Leu Glu
145                 150                 155                 160
Asn Thr Thr Phe Asn Ser Ser Glu Ala Glu Gln Lys Thr Gln Arg
                165                 170                 175
Phe Tyr Leu Ser Cys Leu Gln Val Glu Arg Ile Glu Glu Leu Gly Ala
                180                 185                 190
Gln Pro Leu Arg Asp Leu Ile Glu Lys Ile Gly Gly Trp Asn Ile Thr
            195                 200                 205
Gly Pro Trp Asp Gln Asp Asn Phe Met Glu Val Leu Lys Ala Val Ala
        210                 215                 220
Gly Thr Tyr Arg Ala Thr Pro Phe Phe Thr Val Tyr Ile Ser Ala Asp
225                 230                 235                 240
Ser Lys Ser Ser Asn Ser Asn Val Ile Gln Val Asp Gln Ser Gly Leu
                245                 250                 255
Phe Leu Pro Ser Arg Asp Tyr Tyr Leu Asn Arg Thr Ala Asn Glu Lys
                260                 265                 270
Val Leu Thr Ala Tyr Leu Asp Tyr Met Glu Glu Leu Gly Met Leu Leu
            275                 280                 285
Gly Gly Arg Pro Thr Ser Thr Arg Glu Gln Met Gln Gln Val Leu Glu
        290                 295                 300
Leu Glu Ile Gln Leu Ala Asn Ile Thr Val Pro Gln Asp Gln Arg Arg
305                 310                 315                 320
Asp Glu Glu Lys Ile Tyr His Lys Met Ser Ile Ser Glu Leu Gln Ala
                325                 330                 335
Leu Ala Pro Ser Met Asp Trp Leu Glu Phe Leu Ser Phe Leu Leu Ser
            340                 345                 350
Pro Leu Glu Leu Ser Asp Ser Glu Pro Val Val Val Tyr Gly Met Asp
        355                 360                 365
Tyr Leu Gln Gln Val Ser Glu Leu Ile Asn Arg Thr Glu Pro Ser Ile
    370                 375                 380
Leu Asn Asn Tyr Leu Ile Trp Asn Leu Val Gln Lys Thr Ser Ser
385                 390                 395                 400
Leu Asp Arg Arg Phe Glu Ser Ala Gln Glu Lys Leu Leu Glu Thr Leu
                405                 410                 415
Tyr Gly Thr Lys Lys Ser Cys Val Pro Arg Trp Gln Thr Cys Ile Ser
            420                 425                 430
Asn Thr Asp Asp Ala Leu Gly Phe Ala Leu Gly Ser Leu Phe Val Lys
        435                 440                 445
Ala Thr Phe Asp Arg Gln Ser Lys Glu Ile Ala Glu Gly Met Ile Ser
    450                 455                 460
```

-continued

```
Glu Ile Arg Thr Ala Phe Glu Glu Ala Leu Gly Gln Leu Val Trp Met
465                 470                 475                 480

Asp Glu Lys Thr Arg Gln Ala Ala Lys Glu Lys Ala Asp Ala Ile Tyr
                485                 490                 495

Asp Met Ile Gly Phe Pro Asp Phe Ile Leu Glu Pro Lys Glu Leu Asp
            500                 505                 510

Asp Val Tyr Asp Gly Tyr Glu Ile Ser Glu Asp Ser Phe Phe Gln Asn
        515                 520                 525

Met Leu Asn Leu Tyr Asn Phe Ser Ala Lys Val Met Ala Asp Gln Leu
    530                 535                 540

Arg Lys Pro Pro Ser Arg Asp Gln Trp Ser Met Thr Pro Gln Thr Val
545                 550                 555                 560

Asn Ala Tyr Tyr Leu Pro Thr Lys Asn Glu Ile Val Phe Pro Ala Gly
                565                 570                 575

Ile Leu Gln Ala Pro Phe Tyr Ala Arg Asn His Pro Lys Ala Leu Asn
            580                 585                 590

Phe Gly Gly Ile Gly Val Val Met Gly His Glu Leu Thr His Ala Phe
        595                 600                 605

Asp Asp Gln Gly Arg Glu Tyr Asp Lys Glu Gly Asn Leu Arg Pro Trp
    610                 615                 620

Trp Gln Asn Glu Ser Leu Ala Ala Phe Arg Asn His Thr Ala Cys Met
625                 630                 635                 640

Glu Glu Gln Tyr Asn Gln Tyr Gln Val Asn Gly Glu Arg Leu Asn Gly
                645                 650                 655

Arg Gln Thr Leu Gly Glu Asn Ile Ala Asp Asn Gly Gly Leu Lys Ala
            660                 665                 670

Ala Tyr Asn Ala Tyr Lys Ala Trp Leu Arg Lys His Gly Glu Glu Gln
        675                 680                 685

Gln Leu Pro Ala Val Gly Leu Thr Asn His Gln Leu Phe Phe Val Gly
    690                 695                 700

Phe Ala Gln Val Trp Cys Ser Val Arg Thr Pro Glu Ser Ser His Glu
705                 710                 715                 720

Gly Leu Val Thr Asp Pro His Ser Pro Ala Arg Phe Arg Val Leu Gly
                725                 730                 735

Thr Leu Ser Asn Ser Arg Asp Phe Leu Arg His Phe Gly Cys Pro Val
            740                 745                 750

Gly Ser Pro Met Asn Pro Gly Gln Leu Cys Glu Val Trp
        755                 760                 765
```